US012766288B2

(12) United States Patent
Lazarovich

(10) Patent No.: US 12,766,288 B2
(45) Date of Patent: Oct. 20, 2026

(54) METHODS AND SYSTEMS OF PAVLOVIAN SLEEP INDUCTION

(71) Applicant: REMmedy Inc., Stowe, VT (US)

(72) Inventor: Mark Lazarovich, Stowe, VT (US)

(73) Assignee: REMmedy Inc., Stowe, VT (US)

( * ) Notice: Subject to any disclaimer, the term of this patent is extended or adjusted under 35 U.S.C. 154(b) by 1116 days.

(21) Appl. No.: 17/845,108

(22) Filed: Jun. 21, 2022

(65) Prior Publication Data

US 2022/0313945 A1 Oct. 6, 2022

Related U.S. Application Data

(63) Continuation-in-part of application No. 16/568,627, filed on Sep. 12, 2019, now Pat. No. 11,369,771.

(60) Provisional application No. 62/749,746, filed on Oct. 24, 2018.

(51) Int. Cl.
*A61M 21/02* (2006.01)
*A61M 21/00* (2006.01)

(52) U.S. Cl.
CPC ..... *A61M 21/02* (2013.01); *A61M 2021/0016* (2013.01); *A61M 2205/3303* (2013.01)

(58) Field of Classification Search
CPC .... A61M 21/00–02; A61M 2021/0016; A61B 5/4806–4812
See application file for complete search history.

(56) References Cited

U.S. PATENT DOCUMENTS

| | | | |
|---|---|---|---|
| 5,023,020 | A | 6/1991 | Machida et al. |
| 5,318,503 | A | 6/1994 | Lord |
| 6,702,767 | B1 | 3/2004 | Douglas |
| 6,866,041 | B2 | 3/2005 | Hardy, Jr. et al. |
| 9,434,907 | B2 | 9/2016 | Jeon et al. |
| 9,511,166 | B1 | 12/2016 | Li |
| 9,839,762 | B2 | 12/2017 | Berg et al. |
| 2005/0185398 | A1 | 8/2005 | Scannell, Jr. |

(Continued)

FOREIGN PATENT DOCUMENTS

| | | |
|---|---|---|
| WO | 2018108582 | 5/2018 |

OTHER PUBLICATIONS

Tanaka et al., "Statistical Features of Hypnagogic EEC Measured by a New Scoring System", 1976; Sleep, 19(9): 731-738.

*Primary Examiner* — Thaddeus B Cox
(74) *Attorney, Agent, or Firm* — CALDWELL LLC

(57) ABSTRACT

A Pavlovian conditioned reflex sleep induction kit includes at least one physiological sensor, wherein the at least one physiological sensor is configured to detect at least a physiological parameter of a user and transmit a detection signal to an automatically activated scent diffuser, wherein the automatically activated scent diffuser is configured to receive an electronic activation signal and to diffuse a scent as a function of the electronic activation signal, a control circuit configured to receive the detection signal from the at least one physiological sensor, to ascertain that the user is entering a hypnagogic state, and to transmit the electronic activation signal to the automatically activated scent diffuser, thereby conditioning the user to respond to subsequent sensing of the same scent. For later use, a user-activated scent diffuser is provided, that diffuses the same scent upon activation by a user, to thereby trigger the conditioned reflex to fall asleep.

20 Claims, 15 Drawing Sheets

(56) References Cited

U.S. PATENT DOCUMENTS

| | | | | |
|---|---|---|---|---|
| 2006/0106275 | A1* | 5/2006 | Raniere ................. | A61M 21/02 600/26 |
| 2007/0207220 | A1 | 9/2007 | Luedtke et al. | |
| 2010/0309434 | A1 | 12/2010 | Van Schijndel et al. | |
| 2011/0015500 | A1 | 1/2011 | Wu | |
| 2011/0160619 | A1 | 6/2011 | Gabara | |
| 2012/0272958 | A1* | 11/2012 | Arzi .................... | A61M 15/085 128/203.14 |
| 2015/0190607 | A1 | 7/2015 | Sugio et al. | |
| 2015/0290419 | A1 | 10/2015 | Kare et al. | |
| 2016/0361515 | A1* | 12/2016 | Jung .................. | A61B 5/02055 |
| 2017/0053068 | A1 | 2/2017 | Pillai et al. | |
| 2017/0312476 | A1 | 11/2017 | Woo | |
| 2017/0319816 | A1 | 11/2017 | Sokol et al. | |
| 2017/0361133 | A1 | 12/2017 | Yu et al. | |
| 2018/0050171 | A1 | 2/2018 | Tabert et al. | |
| 2018/0125256 | A1 | 5/2018 | Tsern et al. | |
| 2020/0094013 | A1* | 3/2020 | Kochman .......... | A61B 5/02438 |

* cited by examiner

METHODS AND SYSTEMS OF PAVLOVIAN SLEEP INDUCTION

CROSS-REFERENCE TO RELATED APPLICATIONS

This application is a continuation-in-part of Non-provisional patent application Ser. No. 16/568,627 filed on Sep. 12, 2019, now U.S. Pat. No. 11,369,771, issued on Jun. 28, 2022; and entitled "METHODS AND SYSTEMS OF PAVLOVIAN SLEEP INDUCTION," the entirety of which is incorporated herein by reference, and which claims the benefit of priority of U.S. Provisional Patent Application Ser. No. 62/749,746, filed on Oct. 30, 2018, and titled "METHODS AND SYSTEMS OF PAVLOVIAN SLEEP-INDUCTION," which is incorporated by reference herein in its entirety.

FIELD OF THE INVENTION

The present invention generally relates to the field of technologies to aid in sleep, and to counter insomnia. In particular, the present invention is directed to methods and systems for Pavlovian conditioned reflex sleep induction.

BACKGROUND

Poor sleep has a proven, significantly negative effect on health, well-being, performance, productivity, memory, work satisfaction and mood. For business travelers, consequences of poor sleep can occur at a mission-critical time, when important presentations, meetings and consultations are planned. A 2017 survey of business travelers in the United States documented that 36% of them experienced trouble sleeping in hotels. A 2019 survey documented that 80% of travelers have trouble sleeping, when away from home. Similar situational forms of insomnia can affect airline pilots and crews, shift workers, and professional athletes. Existing solutions to this problem include various devices, relying on use of stimuli intended to induce sleep, and pharmacological solutions. The former solutions rely on purported sleep-inducing properties of the stimuli in question, as evidenced by tenuous and uncertain study results regarding such sleep-inducing effects. The latter solutions vary from relatively ineffective compounds to compounds with significant and well-documented side-effects such as residual drowsiness, lethargy, hangover, tired, sluggish, and/or exhaustive feelings during wake hours, as well as dependency. The use of so-called "sleeping pills" can be associated with stigma for the user.

SUMMARY OF THE DISCLOSURE

In an aspect, a system for inducing a Pavlovian conditioned reflex association of a scent with sleep initiation, the system including at least a physiological sensor, wherein the at least a physiological sensor is configured to detect at least a physiological parameter of a user and to transmit a detection signal, a control circuit configured to receive the detection signal from the at least a physiological sensor, determine that the user is entering a hypnagogic state, and transmit an electronic activation signal. The system further includes an automatically activated scent diffuser, wherein the automatically activated scent diffuser is configured to receive the electronic activation signal. The automatically activated scent diffuser includes a housing, the housing including a compartment, wherein the compartment comprises a scent-diffusing material, a diffusing vent aperture disposed on the housing, wherein the diffusing vent aperture is in communication with the compartment, a shutter rotatably mounted to housing, wherein the shutter has a first position wherein the shutter opens the diffusing vent aperture and the shutter has a second position wherein the shutter closes the diffusing vent aperture, and a linear actuator is configured to move the shutter between the first position and the second position in response to receiving the electronic activation signal.

In another aspect, a method for inducing a Pavlovian conditioned reflex association of a scent with sleep initiation, the method including detecting at least a physiological parameter of a user using at least a physiological sensor, transmitting, by the physiological sensor, a detection signal, receiving, by a control circuit, the detection signal from the at least a physiological sensor, determining, by the control circuit, that the user is entering a hypnagogic state, transmitting, by the control circuit, an electronic activation signal to an automatically activated scent diffuser receiving, by the automatically activated scent diffuser, the electronic activation signal, and moving a shutter, by a linear actuator, between a first position and a second position in response to receiving the electronic activation signal. The manually activated scent diffuser includes a housing, the housing comprising a compartment, wherein the compartment comprises a scent-diffusing material, a diffusing vent aperture disposed on the housing, wherein the diffusing vent aperture is in communication with the compartment, the shutter rotatably mounted to housing, wherein the shutter has the first position wherein the shutter opens the diffusing vent aperture and the shutter has the second position wherein the shutter closes the diffusing vent aperture, and the linear actuator.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

In an embodiment, this disclosure describes systems and methods for creating Pavlovian or conditioned reflex association between sleep entry and a scent. At least one physiological sensor may detect one or more physiological parameters of a user, which may be used by a control circuit such as a microprocessor or mobile device to identify a moment when the user is beginning to fall asleep. A control circuit may cause a scent diffuser to release a scent upon detection, which user may smell on a plurality of occasions while falling asleep, thereby creating a Pavlovian association between falling asleep and the scent. A kit, including a user-activated scent diffuser, may subsequently be used by the user to aid in falling asleep; since the user-activated scent diffuser need not communicate with sensors or other equipment to work, the user may be able to carry it anywhere, and use it in any circumstances under which the user wishes to sleep.

Figure 1:
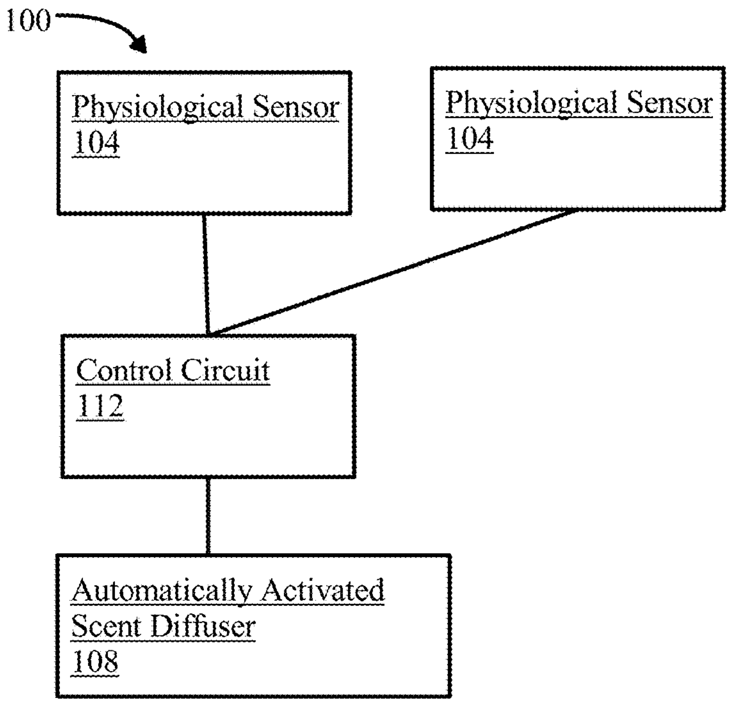
FIG. 1 is a block diagram illustrating an exemplary embodiment of a system for inducing a Pavlovian conditioned reflex association of a scent with initiation of sleep.

Referring now to FIG. 1, an exemplary embodiment of a system 100 is illustrated, for inducing a Pavlovian or conditioned reflex association of a scent with sleep initiation. System 100 includes at least a physiological sensor 104. At least a physiological sensor 104 may be any device or component that measures a physiological parameter of a user and generates an electrical signal as a function of the measurement. At least a physiological parameter may include any information that may be sensed from user's body, including without limitation any electrical, chemical, optical, auditory, olfactory, kinetic, or other information; at least a physiological parameter may include, without limitation, galvanic skin response or skin conductance response, pulse rate, breathing rate, blood flow, heartbeat signatures, electrolyte type and/or concentration, blood metabolite levels or ratios, blood pH level, position and/or balance, body strain, neurological functioning, brain activity, brain waves, blood pressure, cranial pressure, hydration level, auscultatory information, skin and/or core body temperature, facial emotions, eye muscle movement, body movement, blood volume, inhaled and/or exhaled breath volume, exhaled breath physical and/or chemical composition, reflex response sleepiness, response to external stimuli, swallowing volume, swallowing rate, head position or tilt, internal body sounds, functional near-infrared spectroscopy signals, snoring, and/or other physiological information. Various non-limiting examples of such parameters are described in further detail in this disclosure with regard to exemplary categories and/or embodiments of at least a physiological sensor 104.

Still referring to FIG. 1, at least a physiological sensor 104 may include, without limitation, at least an electrophysiologic sensor, defined herein as a sensor that detects at least an electrical, magnetic, or electromagnetic parameter, state, or reading regarding body of user. At least an electrophysiologic sensor may include an electrodynamic sensor device configured to sense an electrical activity of the heart of a subject. For example, the electrodynamic sensor may be configured to sense a heart rate or heart rate variability pattern using electrical activity of the heart, for instance using electrocardiography (ECG or EKG), or conductivity. Electrocardiography may include a process of recording electrical activity of a heart over a period of time using electrodes placed on the skin; electrodes may detect tiny electrical changes on the skin that arise from a heart muscle's electrophysiologic pattern of depolarizing during each heartbeat. An ECG may be used to measure rate and rhythm of heartbeats or other patterns relating to heartbeats, including without limitation heart rate variability (HRV) patterns. Electrodes may be placed in contact with the user's skin using any suitable means, including adhesion or incorporation in a wearable device such as a band of elastic material around user's torso, that places electrodes in contact with user's skin. In some embodiments, direct contact may not be necessary, and electrical functioning may be monitored capacitively, inductively, electromagnetically, optically, or a combination of these approaches. Persons having ordinary skill in the art, upon reviewing the entirety of this disclosure, will be aware of various ways in which EKG data may be collected, consistent with the instant disclosure.

With continued reference to FIG. 1, at least an electrophysiologic sensor may include a sensor that monitors neurological functioning. As a non-limiting example, electrophysiologic sensor may include one or more sensors that perform an electroencephalogram (EEG); EEG may involve detection of patterns, such as brain waves, otherwise known as neural oscillations. EEG may be performed by detection of electrical patterns in neural activity using electrodes contacting a user's cranium, such as electrodes placed along a forehead of user. Electrodes may be adhered to user or incorporated in a wearable device, such as without limitation an earpiece or item of headgear placing electrodes at cranial locations such as a forehead or temple. In some embodiments, direct contact may not be necessary, and neurological functioning can be monitored capacitively, inductively, electromagnetically, or a combination of these approaches. In some embodiments, brain waves may couple with low frequency acoustical sensors integrated into a head-mounted module, or the like. Persons having ordinary skill in the art, upon reviewing the entirety of this disclosure, will be aware of various ways in which EEG data may be collected, consistently with the instant disclosure.

Continuing to view FIG. 1, at least an electrophysiologic sensor may include a sensor configured to perform an electrooculogram (EOG); EOG may be defined as an electrophysiologic measurement of eye motion. EOG may be collected using electrodes mounted at or near user's eyes, for instance through use of a mask or other wearable device that contacts the user's eyelids or rests nearby. EOG may be detected through contactless means such as capacitive, inductive, or electromagnetic detection. Alternatively or additionally, at least an electrophysiologic sensor may include electrodes or other sensors for monitoring an electromyogram (EMG) signal measuring electrical activity of muscles or muscular tissue of a user. At least an electrophysiologic sensor may include an electrodermal activity (EDA) sensor, also known as skin conductance, galvanic skin response (GSR) sensor, electrodermal response (EDR) sensor, or the like, which may measure continuous variation in electrical characteristics of skin.

Still viewing FIG. 1, at least a physiological sensor 104 may include one or more sensors configured to detect arterial or vascular data. For instance and without limitation, at least a physiological sensor 104 may include a photoplethysmography (PPG) sensor, which may sense the body's rate of blood flow using a light-based technology whereby a light source is emitted through or at tissue containing blood vessels, and light reflected by or transmitted through the tissue is measured. At least a physiological sensor 104 may include an impedance plethysmograph for measuring changes in volume within an organ or body (usually resulting from fluctuations in the amount of blood or air it contains). For example, an impedance plethysmograph to monitor blood pressure in real-time. At least a physiological sensor 104 may include a sensor to detect pulse oximetry, where pulse oximetry is a standard noninvasive technique of estimating blood gas levels. Pulse oximeters typically employ two or more optical wavelengths to estimate the ratio of oxygenated to deoxygenated blood. Similarly, various types of hemoglobin, such as methemoglobin and carboxyhemoglobin may be differentiated by measuring and comparing the optical absorption at key red and near-infrared wavelengths. Additional wavelengths may be incorporated and/or replace conventional wavelengths. For example, by adding additional visible and infrared wavelengths, myoglobin, methemoglobin, carboxyhemoglobin, bilirubin, SpCO.sub.2, and blood urea nitrogen (BUN) may be estimated and/or monitored in real-time in addition to the conventional pulse oximetry.

With continued reference to FIG. 1, at least a physiological sensor 104 may monitor blood pressure, using, as a non-limiting example, a digital blood pressure monitor; digital blood pressure monitor may include actuators and sonic and pressure transducers placed on the skin, and may measure systolic and/or diastolic pressure, for instance by monitoring a pressure at which a "Korotkoff sound" is first heard (systolic), then disappears (diastolic). This technique may also be used to monitor intra-cranial pressure and other internal pressures. Blood pressure may also be measured by comparing the time between pulses at different regions of the body. At least a physiological sensor 104 may alternatively or additionally include pyroelectric sensor for monitoring heart rate, heart rate variability (HRV) patterns, and the like.

Still referring to FIG. 1, at least a physiological sensor 104 may include a body temperature sensor, which may be any sensor that acquires a temperature of user's body or a portion thereof. Temperature sensor may include, without limitation one or more infrared sensors, which may be composed of thermoelectric/pyroelectric materials or semiconductor devices, such as photodiodes or photoconductors, thermistors, thermocouples, or any other elements or components used in digital and/or electric thermometers or other temperature sensors. Temperature sensor may detect a skin temperature at one or more locations on user's body. Temperature sensor may contact user, or may detect user temperature remotely, for instance by capturing infrared radiation.

Continuing to refer to FIG. 1, at least a physiological sensor 104 may include at least a motion sensor. At least a motion sensor may include at least a gyroscope, which may detect orientation changes of the at least a gyroscope; multiple gyroscopes may detect orientation changes with respect to multiple axes, such as three gyroscopes to detect orientation changes with respect to three axes of rotation, or the like. At least a motion sensor may include at least an accelerometer, such as one or more microelectromechanical systems (MEMS) devices. An accelerometer may measure acceleration or position in two or more axes; alternatively or additionally, at least an accelerometer may include a plurality of accelerometers to detect acceleration with respect to a plurality of axes, such as without limitation three accelerometers that detect motion with regard to three dimensional axes. At least a motion sensor may include an inertial measurement unit (IMU), which may include multiple types of motion sensors in a single chip or system. At least a motion sensor may be mounted to one or more parts of user's body to detect motion thereof. Changes in patterns in user motion may indicate a transition by user from one state of wakefulness or sleep to another state; for instance, a step towards a deeper sleep state or in a direction transitioning from waking to sleep, as described in further detail below, and may be accompanied by a decrease in or cessation of movement by user, and/or by an increased regularity of chest movements indicating regular breathing in a pattern indicative of incipient slumber.

As a further non-limiting example, and still referring to FIG. 1, at least a physiological sensor 104 may include at least a camera. At least a camera may be any electronic device capable of capturing light, whether in visible or non-visible spectra, and transmitting an electrical signal based on the detection. At least a camera may, as a non-limiting example, capture an eye area of a user, to ascertain, based on the analysis of the captured images, whether or not an eye movement occurs; when the eye stops, for instance, the user's sleep state may be determined to be rapid-eye movement (REM) or non-REM sleep state. Similarly, the camera may track user's blink rate, including without limitation user's involuntary blink rate, which may be indicative of increased drowsiness. Camera may detect body movement of user, which may be used similarly to body movements detected by at least a motion sensor; camera may, for instance, capture a sequence of images of user's body and compare images of the sequence of images to determine whether user has moved user's body and, if so, how frequently or to what extent.

Continuing to refer to FIG. 1, at least a physiological sensor 104 may include at least an acoustic sensor, such as a microphone or the like. At least an acoustic sensor may detect and/or monitor breathing characteristics of user, for instance via auscultatory signal extraction. In an embodiment, an acoustic sensor may be used to sense sounds associated with breathing. Signal processing algorithms may then be used to extract breathing sounds from other sounds and noise, for instance using digital signal filtering or noise elimination processes. This information may be used, as a non-limiting example, to measure and/or track intensity, volume, and speed of breathing, which may in turn be used to determine a user's state of wakefulness, state of sleep, or near-sleep condition. Alternatively or additionally, at least a physiological sensor 104 may monitor breathing using employ pressure transducers. For instance, and without limitation, changes in pressure inside or near the ear associated with breathing may be measured directly and, through signal processing, translated into a breathing monitor. Similarly, optical reflection sensors may be used to monitor pressure by monitoring physical changes in the skin or tissues in response to breathing. For monitoring the physical changes of the tympanic membrane in response to breathing, and hence ascertaining breathing rate, an optical signal extraction approach may be employed. As a further non-limiting example, microphones positioned correctly near a sleep surface can sometimes pickup and detect a heartbeat and respiration. Microphones can also hear snoring, coughing, or the like.

Still referring to FIG. 1, at least a physiological sensor 104 is configured to detect at least a physiological parameter of user and transmit a detection signal. Detection signal may be transmitted via wired connection to one or more other elements of system 100 as described below; for instance, and without limitation, at least a physiological sensor 104 may be incorporated in a single electronic device, or mounted on a single chip, with one or other additional components of system 100. Alternatively or additionally, detection signal may be transmitted to one or more components of system 100 wirelessly. For instance, and without limitation, at least a physiological sensor 104 may include one or more wireless transceivers, which may communicate according to protocols such as BLUETOOTH®, ANT+, Wi-Fi, or ZigBee and may be configured to transmit information wirelessly one or more other components of system 100.

Continuing to refer to FIG. 1, system 100 includes an automatically activated scent diffuser 108. Automatically activated scent diffuser 108 is configured to receive an electronic activation signal and diffuse a scent as a function of the electronic activation signal; the automatically activated scent diffuser 108 may be any device that can selectively release a scent into the air, so that user can smell the scent. Scent diffuser may include a scent source, which may include a material that releases scent molecules into the air. Scent molecules may include any molecules that human olfactory receptors detect as having an aroma. Scent molecules may pass through air to a user's nose by diffusion. Scent molecules may have aromas recognizable to users; aromas may include aromas generally considered pleasant, such as the aromas of fruits, flowers, herbs, pine needles, or the like. Scent source may include a material containing one or more volatile materials that either have the desired aroma or carry molecules having the desired aroma in solution. Scent source may include one or more scent wafers, which may release scent upon exposure to air, for instance by evaporation of volatile materials contained within scent wafer. Scent source may include one or more scent liquids, such as perfumes, essential oils, or the like; scent liquids may be volatile, or contain volatile materials, causing diffusion through evaporation. Scent-diffusing material may include a gas. Scent source may be in any other suitable form, including a film, foam, or gel. Scent source may include a material that releases scent molecules under specific circumstances; for instance, scent source may include a wafer, film, liquid, or other material that releases scent only on exposure to heat, electric current, or the like. As a non-limiting example, scent source may contain a mixture or solution of volatile or scent-diffusing material with a substance that seals the scent-diffusing material at a first temperature, such as room temperature, but changes to release scent-diffusing material at a second temperature, which may be a higher temperature; substance may be waxy, may have a structure that encapsulates scent-diffusing material in small envelopes or capsules of material that will open or rupture upon exposure to heat, or may combine with scent-diffusing material via chemical bonds that release upon heat exposure. Alternatively or additionally, substance may be a material that encapsulates or maintains a chemical bond to scent-diffusing material until exposed to an electric current or field. In an embodiment, removal of a release stimulation may result in a cessation of diffusion of scent; for instance, where substance encapsulates scent-diffusing material until exposure to ultrasonic vibration, heat or electric currents and/or fields, cessation of heat, ultrasonic vibration, or electric currents and/or fields may cause substance to re-encapsulate scent-diffusing material. Similarly, chemical bonds that are separated by heat, ultrasonic vibration, and/or electric current and/or fields may reform upon cooling or cessation of the electric stimulus. Heat used to release scent-diffusing material may be applied using an electrical heating element, which may be controlled by a control circuit 112, microprocessor, microcontroller, or the like; electric current and/or field may be similarly provided electrically. Ultrasonic vibration may be applied using any electrically triggered sonic vibration generating component, such as, without limitation, piezoelectric vibrating components. Automatically activated scent diffuser may be located near user's head and/or nose.

Still viewing FIG. 1, scent-diffusing material may be contained in an enclosed container and selectively released. For instance, where scent-diffusing material includes a liquid or gel, scent-diffusing material may be contained in a cartridge, compartment, or bottle-like component that may be sealed until release is desired. Where scent-diffusing material includes a film, foam, or solid object such as a wafer, scent-diffusing material may be stored in a cartridge, wrapper, or compartment that may be selectively opened when scent diffusion is desired. A scent-diffusing gas may similarly be contained in a cartridge or compartment; scent-diffusing gas may be contained under pressure. Selective opening of enclosed container may include piercing a wrapper, opening a selectively closable aperture, or the like. Alternatively or additionally, liquid, gas, or gel may be released from one or more nozzles, such as spray nozzles; nozzles may be mechanically or electrically actuated in any suitable way, including forcing of scent-diffusing material through nozzles using a pump, impeller, or other pressure source, including pressurized cartridges. Nozzles may be actuated by opening a valve. An aperture of enclosed container may be opened by electrically controlled mechanical movement of a door or lid, for instance using an electric motor or linear actuator, a servo, or the like.

Continuing to view FIG. 1, automatically activated scent-diffuser may include one or more dispersal mechanisms. Where nozzles are used, dispersal may be aided in part by pressurized ejection from nozzles. Dispersal mechanisms may similarly include an ultrasonic nebulizer, air-blowing component such as a fan, impeller, pump, or micropump, which causes airflow past scent-diffusing material, carrying it and resulting aromas to user's nose or speeding up diffusion to accomplish the same. Automatically activated scent diffuser 108 may be incorporated in a home heating, ventilation, and/or air-conditioning system, permitting air circulation of such a system to aid in dispersal or diffusion of scent molecules. In an embodiment, where automatically activated scent diffuser 108 includes a heater, the heater may cause air currents through convection, which may have a similar effect to air blowing component. One or more dispersal mechanisms may include additional or alternative components, such as a wick, which may draw scent-diffusing material using capillary action from a container or enclosure to exposure to open air, where evaporation may disperse scent-diffusing material or enclosure to exposure to open air, where evaporation may disperse scent-diffusing material. A dispersal mechanism may include an ultrasonic nebulizer atomizing the scent-diffusing material and dispersing it to open air. Automatically activated scent diffuser may be configured to stop diffusing scent upon reception of a deactivation signal.

Figure 2A:
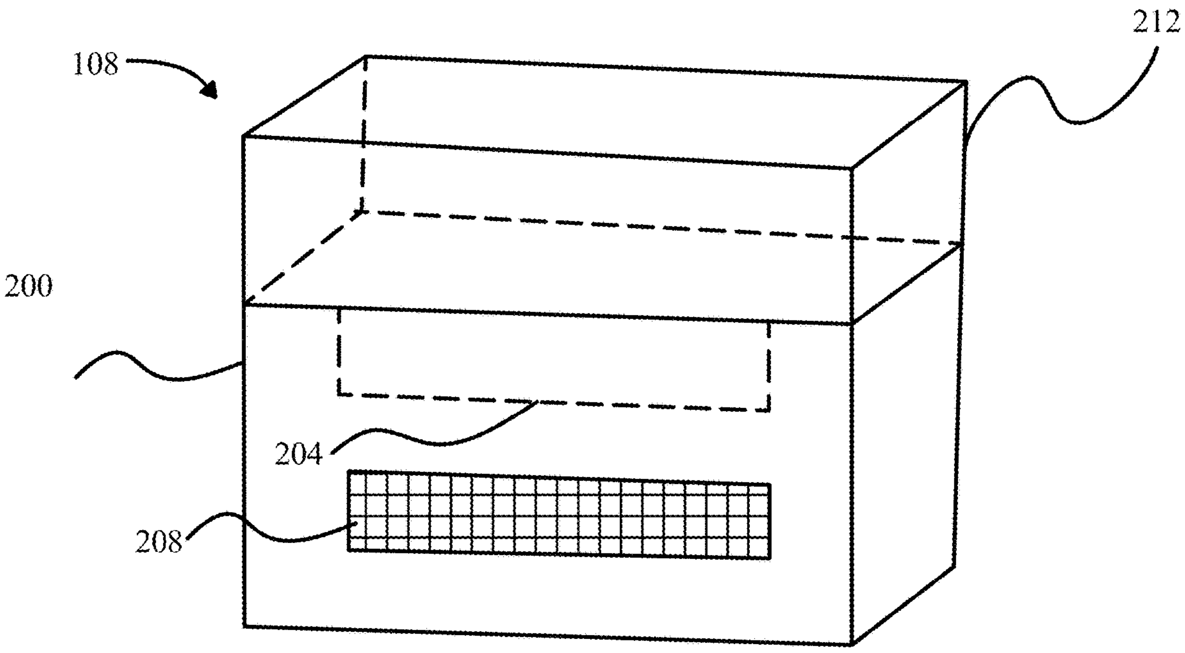
FIG. 2A is a schematic diagram illustrating a perspective view of an exemplary embodiment of an automatically activated scent diffuser.

Referring now to FIG. 2A, an exemplary embodiment of an automatically activated scent diffuser 108 is illustrated. Automatically activated scent diffuser 108 may have a housing 200, which may be in any suitable form, including without limitation a box form. Housing 200 may include an air intake 204, which may include or communicate with an aperture or selectively closable aperture of a compartment containing scent-diffusing material as described above. Housing 200 may include a diffusing vent 208, which may include a grid or other covering; diffusing vent 208 may include or communicate with an aperture or selectively closable aperture of a compartment containing scent-diffusing material as described above. Housing 200 may include a manually activated opening 212, such as a hinged and/or latched lid, which may be used to open housing 200 and/or compartment containing scent-diffusing material; manually activated opening 212 may cause scent release when opened, be used to insert additional scent-diffusing material in automatically activated scent diffuser 108, or the like.

Figure 2B:
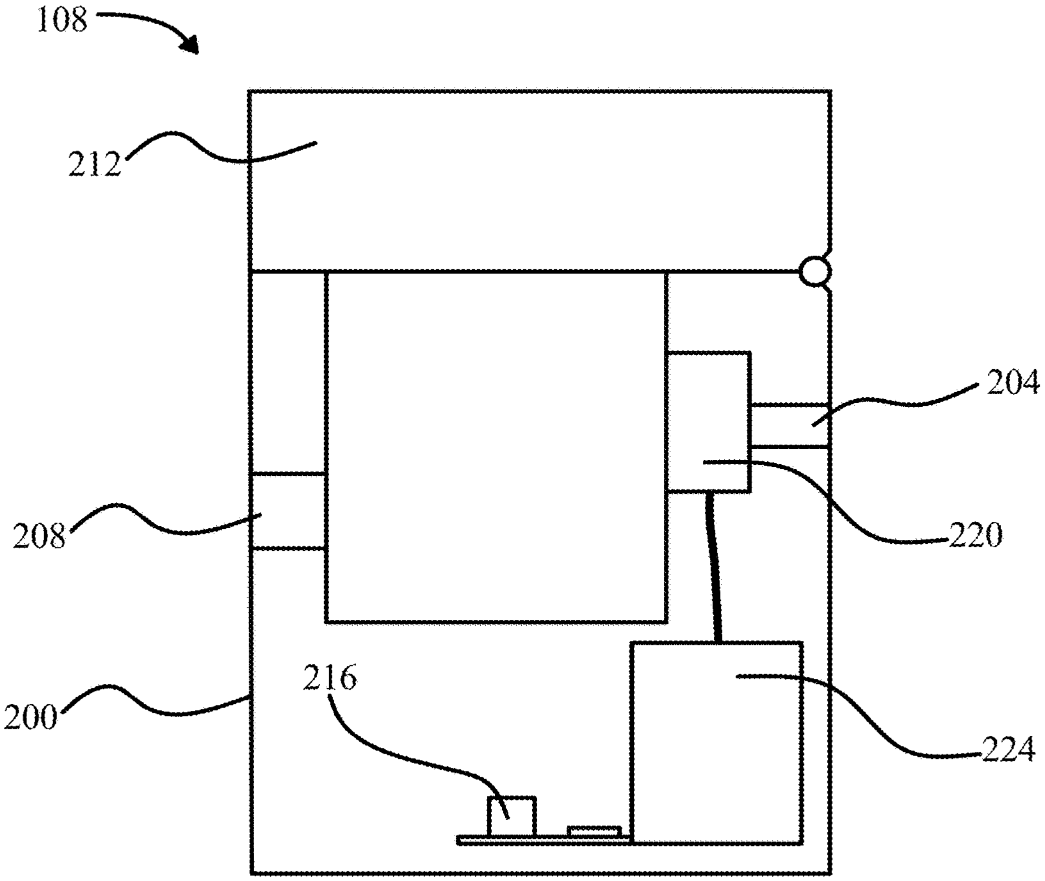
FIG. 2B is a schematic diagram illustrating a cutaway side view of exemplary embodiment of an automatically activated scent diffuser.

Referring now to FIG. 2B, housing 200 may contain one or more components of automatically activated scent diffuser 108 as described above, including a transceiver 216, such as a transceiver as described above, an electronic fan controller, an electric fan 220 with a motor, a battery 224, and the like. Housing 200 may include a receptacle for a scent wafer. Housing 200 may include a power switch.

Still referring to FIG. 2B, in operation, automatically activated scent diffuser 108 may prevent scent diffusion until receipt of an activation signal; for instance, where present, diffusing vent 208 and air intake 204 may be sealed initially, preventing scent dispersal. Upon an electronic activation signal, which may be received via any suitable means, including a signal to transceiver, automatically activated scent diffuser 108 may diffuse scent using any mechanisms, components, or combination thereof; for instance, and without limitation, where automatically activated scent diffuser 108 is as depicted in FIG. 2, an aperture at diffusing vent 208 and/or air intake 204 may be opened and fan may be activated, causing airflow from air intake 204 to diffusing vent 208 to carry scent molecules out into the air, so that user may smell them. In an alternative or additional embodiment, automatically activated scent diffuser 108 may include a scent-diffusing module coupled to, or incorporated into, a mobile device such as, without limitation, an electronic music playback device or a smart phone.

Referring again to FIG. 1, system 100 includes a control circuit 112. Control circuit 112 may include any electronic circuit that may be configured as described below; for instance, control circuit 112 may include a logic circuit incorporating one or more logic gates. Control circuit 112 may include a microprocessor, microcontroller, or any computing device as described below in reference to FIG. 5. As a non-limiting example, control circuit 112 may include a mobile computing device such as a "smartphone" or the like. Control circuit 112 may be communicatively connected to automatically activated scent diffuser 108 and/or at least a physiological sensor 104, where "communicative connection" is defined as a relationship between two or more devices or components whereby the two or more devices or components are capable of sending and/or receiving electrical or wireless signals to and/or from each other; for instance, where automatically activated scent diffuser 108 includes a transceiver or other wireless communication device, control circuit 112 may include a transceiver or other wireless communication device capable of communication with the transceiver or other wireless communication device of the automatically activated scent diffuser 108. Alternatively or additionally, control circuit 112 may be connected to automatically activated scent diffuser 108 and/or other components via a wired connection, by way of one or more intermediate devices, or by incorporation in the same component, chip, or circuit as automatically activated scent diffuser 108. Control circuit 112 may be configured to perform any methods or method steps as disclosed herein in any combination, including without limitation method 400 as described in further detail below. As a non-limiting example, control circuit 112 may be configured to receive a detection signal from the at least a physiological sensor 104, determine that the user is entering a hypnagogic state, and transmit the electronic activation signal to the automatically activated scent diffuser 108, as described in further detail below.

Figure 3:
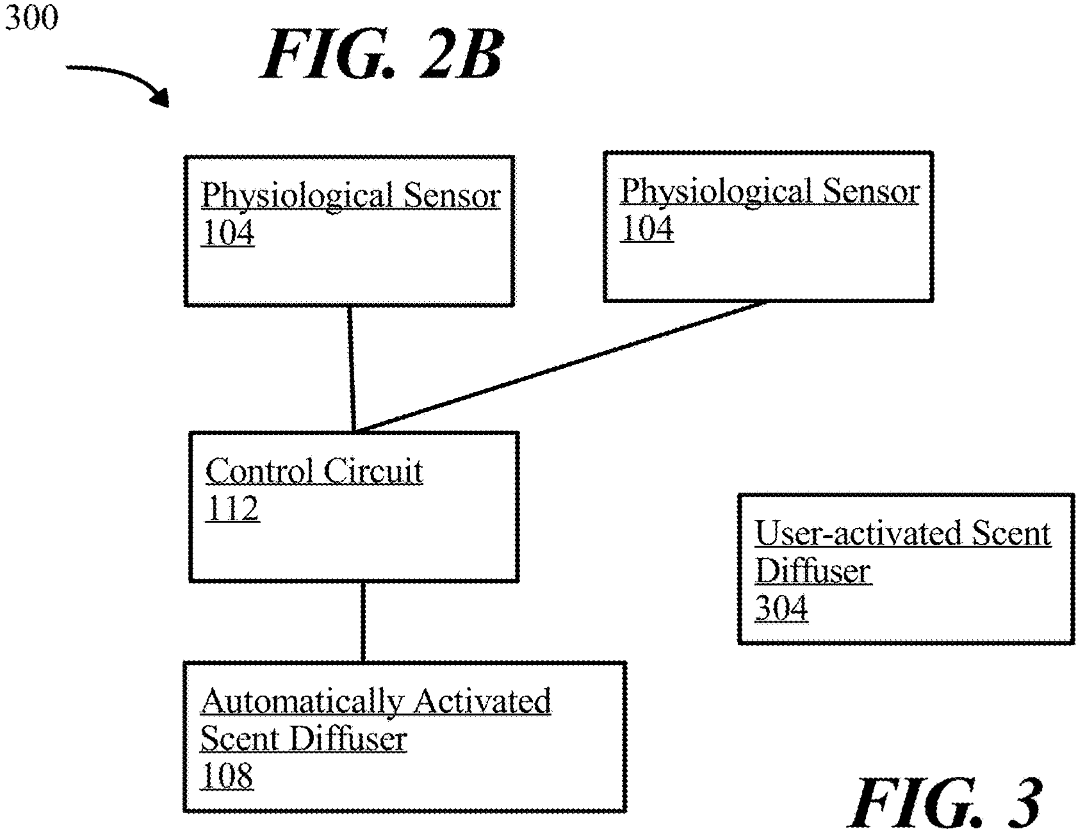
FIG. 3 is a block diagram illustrating an exemplary embodiment of a Pavlovian sleep-induction kit for inducing a Pavlovian association of a scent with sleep initiation.

Referring now to FIG. 3, an exemplary embodiment of a Pavlovian conditioned reflex sleep induction kit 300 is illustrated. In an embodiment, kit 300 includes at least a physiological sensor 104 configured to detect at least a physiological parameter of a user and transmit a detection signal; this may be implemented using any components, devices, or processes described above in reference to FIG. 1. Kit 300 includes an automatically activated scent diffuser 108 configured to receive an electronic activation signal and diffuse a scent, in response to the electronic activation signal; this may be implemented using any components, devices, or processes described above in reference to FIG. 1. Kit 300 includes a control circuit 112 configured to receive the detection signal from the at least a physiological sensor 104, determine that the user is entering a hypnagogic state, and transmit the electronic activation signal to the automatically activated scent diffuser 108. Control circuit 112 may be implemented and/or configured using any components, devices, or processes described above in reference to FIG. 1.

Still referring to FIG. 3, kit 300 includes a user-activated scent diffuser 304 that diffuses the scent upon activation by a user. User-activated scent diffuser 304 may include a scent diffuser that diffuses scent upon activation by user; activation by user, as used herein, means direct activation by a voluntary act on the part of the user, in a process that does not include sensing physiological parameters or determining a user state. For instance, user-activated scent diffuser 304 may include a switch that user turns on, causing release of scent, a manually activated opening 212, such as without limitation manually activated opening 212 depicted in FIG. 2, which exposes scent-diffusing material, a heat source such as a candle or an electric heater that user can apply to substance containing scent-diffusing material, a vibration-generating component to generate ultrasonic vibrations, or the like. User-activated scent diffuser 304 may include a container, such as a portable container, that user may open and/or close manually; container may be constructed of any suitable material, including plastic, paper, metal, wood, or the like. Container may have a form of a box or wrapper that user opens to release scent. In a non-limiting example, user-activated scent diffuser 304 may include a container such as a box, wrapper, or sealed packet containing a scent wafer as described above, which user may activate by opening the container, and may deactivate by shutting or sealing the container. User-activated scent diffuser 304 may include any mechanism for scent diffusion and/or dispersal described above for automatically activated scent diffuser 108. User-activated scent diffuser 304 may be a separate device from automatically activated scent diffuser; alternatively, automatically activated scent diffuser 108 may function as user-activated scent diffuser by incorporation of one or more controls or features enabling user to activate scent diffusion, for example manually. Scent diffused by user-activated scent diffuser 304 may be identical, or substantially identical, to scent diffused by automatically activated scent diffuser 108. User-activated scent diffuser 304 may include a scent-diffusing module coupled to, or incorporated into, a mobile device such as, without limitation, a smart phone.

Figure 4:
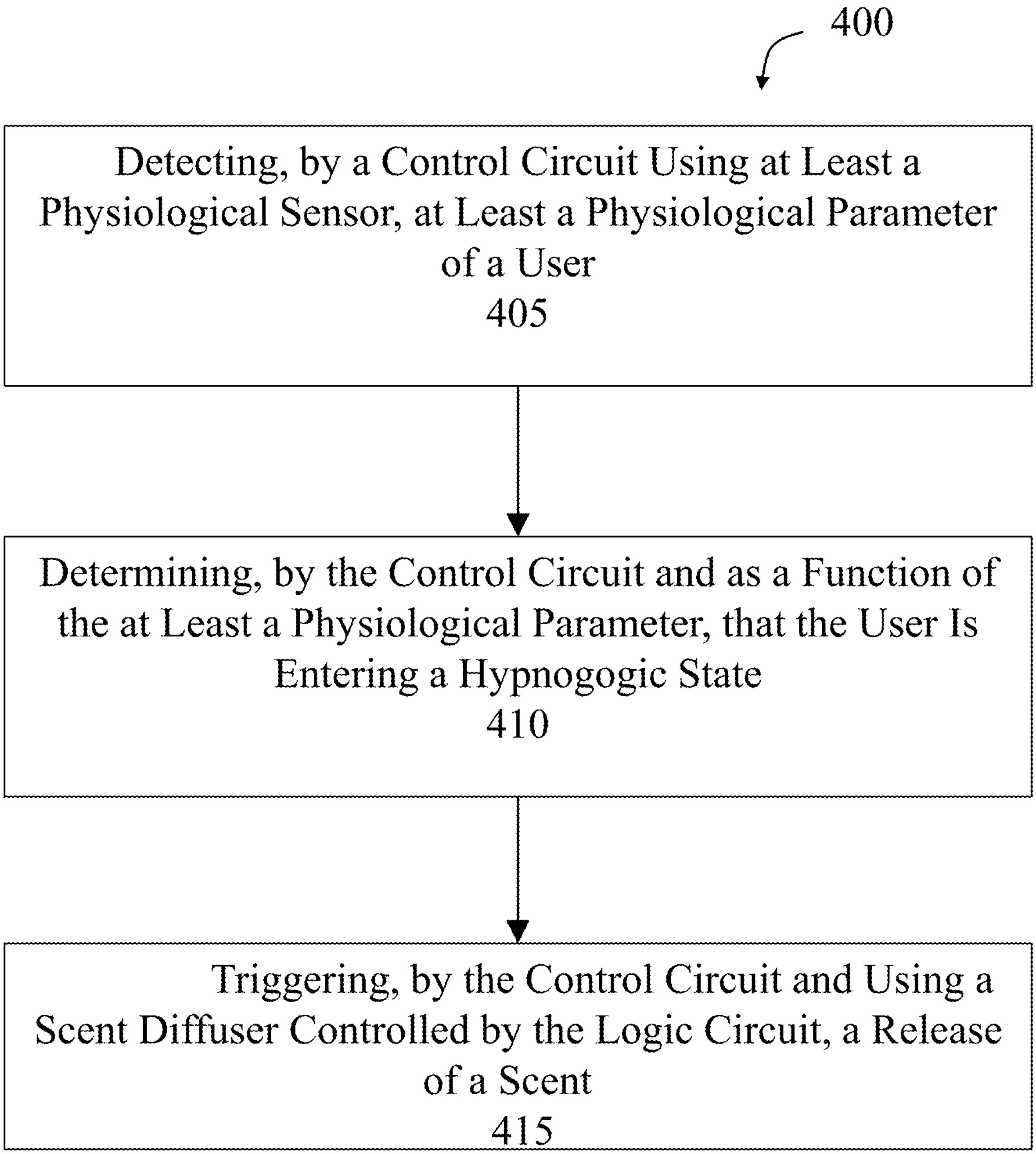
FIG. 4 is a flow diagram illustrating an exemplary embodiment of a method of inducing a Pavlovian association of a scent with sleep initiation.

Referring now to FIG. 4, an exemplary embodiment of a method 400 of inducing a Pavlovian association of a scent with sleep initiation is illustrated. At step 405, control circuit 112 detects, using at least a physiological sensor 104, at least a physiological parameter of a user. Detection may be performed using any processes, process steps, and/or components, in any combination, as described above in reference to FIG. 1.

At step 410, and still referring to FIG. 4, control circuit 112 determines, as a function of the at least a physiological parameter, that the user is entering a hypnagogic state. A "hypnagogic state," as used herein, is a state wherein a user is in the process of transitioning from waking to sleeping; a user in a hypnagogic state may be neither fully awake nor fully asleep. A hypnagogic state may be state of sleep latency, of imminent sleep, or the like. In an embodiment, detection of user entry into hypnagogic state enables control circuit 112 to target scent diffusion to that state, allowing a precise Pavlovian association between sleep entry and diffused scent to be established; this may be crucial to avoid incorrect associations being formed with, for example, wakefulness, including even drowsy wakefulness under circumstances in which user is trying and failing to fall asleep, or with a state after user has fallen asleep.

In an embodiment, and still viewing FIG. 4, determining that user is entering a hypnagogic state may further include determining that at least a physiological parameter indicates a state of pre-sleep relaxation, and estimating a time from pre-sleep relaxation to a hypnagogic state. Indication of pre-sleep relaxation may include detection of a change in neural oscillations, such as a detection of decreasing alpha waves, also known as Berger's waves (neural oscillations in the range of 735-12.5 Hertz); as a further non-limiting example, an increase in beta waves, characterized by frequencies on the order of 13-30 Hertz may be an indication of pre-sleep relaxation. Detection of delta waves, having frequencies ranging from 1-4 Hertz, may alternatively or additionally indicate entry into pre-sleep relaxation. Similarly, a decrease in heart rate, pulse rate, blood pressure, a change in Heart Rate Variability pattern, or another cardiovascular indicator may be compared with values associated with pre-sleep relaxation. In an embodiment, control circuit 112 may track patterns of physiological parameters and timing thereof relative to entry into an identifiable sleep stage. Thus, for instance, a detection of non-REM sleep, REM sleep, or other sleep stages as described below may be used to identify a moment that user has fallen asleep; patterns of physiological indicators such as neural oscillations and/or heart rate, including without limitation heart rate variability (HRV) patterns, may be associated with a time proximal to such detection and may be recorded in memory of control circuit 112. Patterns may be detected by any suitable method for detection of statistical or mathematical relationships, including without limitation machine-learning algorithms such as linear or polynomial regression algorithms. Patterns may be detected using data of a particular user associated with a particular implementation of system 100, and/or using data of multiple users. Control circuit 112 may include, in memory of control circuit 112, an average time from detection of indication of pre-sleep relaxation to detection of entry into a sleep state; average time may be calculated using any modeling or statistical correlation program suitable for detection of patterns of at least a physiological parameter associated with pre-sleep relaxation. In an embodiment, entry into a hypnagogic state may be estimated as occurring at a point between indication of pre-sleep relaxation and a time average time after indication of entry into sleep state, including without limitation a time just before predicted time of entry into sleep state.

Continuing to view FIG. 4, in an embodiment, determining that the user is entering a hypnagogic state may include detecting a first physiological parameter of the at least a physiological parameter at a first time, detecting a second physiological parameter of the at least a physiological parameter at a second time subsequent to the first time, and determining that the second physiological parameter indicates a greater degree of relaxation than the first physiological parameter. Each of first physiological parameter and second physiological parameter may include any physiological parameter as described above in reference to FIGS. 1-3, including without limitation neural oscillations, heart rate, heart rate variability (HRV) patterns, breathing rate, and the like. Association of first physiological parameter and second physiological parameter with greater and/or lesser degrees of relaxation may be determined using any method as described above; a greater degree of relaxation, for instance, may be associated with a physiological parameter typically detected closer in time to detection of a sleep state, while a lesser degree of relaxation may be associated with a physiological parameter typically detected a greater amount of time prior to detection of a sleep state. As a non-limiting, illustrative example, a decrease in alpha waves may typically be detected ten minutes before detection of a sleep state, while an increase in beta waves may typically be detected five minutes before detection of a sleep state; delta waves may typically be detected two minutes before detection of sleep state. This process may be repeated more than once, with more than one physiological parameter functioning as first or second physiological parameter in the above example.

In an embodiment, and continuing to refer to FIG. 4, detection of entry into hypnagogic state may include detection of a physiological parameter correlated with entry into hypnagogic state. For instance, where a physiological parameter is nearly always detected as occurring just before detection of a sleep state, such as delta wave activity beginning two minutes before detection of non-REM sleep, determination of entry into hypnagogic state may include detection of physiological parameter and identification of entry into hypnagogic state at the time of detection.

Still referring to FIG. 4, determination that user is entering hypnagogic state may include one or more determinations that user is in a sleep state; for instance, as noted above determination of sleep states on earlier occasions may be used to estimate a moment of entry into a hypnagogic state, or to identify a physiological indicator consistent with entry into a hypnagogic state. In embodiment, determination of sleep phase by monitoring an individual during sleep may be referred to as sleep staging. Sleep staging may be performed, as a non-limiting example using the traditional Rechtschaffen & Kales rules, which classify sleep into six separate stages: wake, rapid eye movement (REM) sleep, S1 (light sleep), S2 (light sleep), S3 (deep sleep), and S4 (deep sleep). Alternative systems for sleep staging may be known to persons skilled in the art. Techniques for monitoring physiological changes associated with different stages of sleep may include, without limitation, EEG recordings of brain activity, EOG recordings of eye movement and ocular muscle contractions, EKG recordings of heart beats, heart rate variability, heart rate or heart rate entropy, respiratory rate, body temperature, eye or body movements (actigraphy). As a non-limiting example, relationships between cardiovascular activity and particular sleep stages may be used to identify sleep stages. Physiological interconnections between user's central nervous system and the autonomic nervous system, such as autonomic cardiovascular control at the sinus node level may permit analysis concerning sleep structure based, as a non-limiting example, on noninvasive analysis of heart rate variability, as detected from the electrocardiogram. Moreover, morphological changes in the cardiac electrical complex may occur during respiratory cycles and body position changes. Power spectral analysis of instantaneous heart rate fluctuations may be used to record and/or track three components: high frequency, low frequency and very low frequency, which may be correlates of autonomic nervous system function. Time frequency decomposition of these fluctuations may permit identification of transient physiological phenomena as they occur during sleep or wakefulness. Such components may display differential profiles in the different sleep stages, allowing for classification of sleep stages from an EKG.

Continuing to view FIG. 4, and as a further non-limiting example, REM sleep may be identified using measurement of eye movements; eye movements as detected using EOG data and/or video footage of eye movements may be compared to eye movements associated with REM sleep. EEG or other neural oscillation data may be used to identify a sleep state; for instance, a high degree of delta-wave activity may be associated with deeper sleep stages, as may a cessation or marked reduction in alpha waves and/or beta waves. Sleep state may further be estimated by one or more additional physiological parameters in combination. For instance, sleep state may be identified using a combination of motion detection, heart rate, heart rhythm, heart rate variability pattern, heart electrophysiologic pattern or motion signature, blood oxygen saturation, temperature, skin temperature, body position, breathing rhythms and/or respiration rate, audio patterns including detection of snoring, and/or skin conductance. Association of one or more physiological parameters with a sleep state may be programmed into memory of control circuit 112 and/or received from another device. Alternatively or additionally, control circuit 112 may associate one or more physiological parameters with sleep state in a similar manner to methods for determining associations described above; for instance, eye-motion detection may determine that user is in REM sleep, and state of physiological parameters at detection of eye motion correlated with REM sleep may be tracked and used to create further associations.

At step 415, and still viewing FIG. 4, control circuit 112 triggers a release of a scent; this may be performed using automatically activated scent diffuser 108, using any component, process step, or combination thereof described above in reference to FIGS. 1-3. In an embodiment, scent is not released until triggering; for instance automatically activated scent diffuser 108 may allow no scent, or substantially no scent, to be released and/or detected except upon receipt of electronic activation signal. In an embodiment, this may ensure that user establishes a Pavlovian correlation between scent and sleep entry; where user is exposed to scent only upon entry into hypnagogic state, user may develop a strong Pavlovian association between scent and the act of falling asleep. This may ensure that future exposure to scent will cause user to fall asleep more quickly. In an embodiment, control circuit may detect that user has entered a sleep state and deactivate automatically activated scent diffuser 108. Alternatively or additionally, control circuit 112 may determine that a time limit has passed and deactivate the automatically activated scent diffuser 108 as a function of the determination. Time limit may be calculated from any suitable event, including activation or entry into a sleep stage such as light sleep, REM sleep, and/or deep sleep, detected as described above. Deactivation may, in an embodiment, prevent Pavlovian association of the smell with waking or other events besides falling asleep.

In operation, and still viewing FIG. 4, method may involve a first period in which steps 405-415 are followed iteratively; for instance, system 100 may be used on a nightly basis for a number of nights to administer scent to user at entry into hypnagogic state, creating an association, via classical conditioning, between the scent and the moment of entry into sleep. User may then employ kit 300 to aid in sleeping; for instance, user may take user-activated scent diffuser 304 while traveling and, at a moment user wishes to sleep, may position user-activated scent diffuser 304 near user and activate scent diffusion. Pavlovian association between scent and sleep entry may cause user to fall asleep more readily than would otherwise be possible, particularly in unfamiliar settings. Kit 300 may advantageously prevent user from having to carry and/or use sensors or other materials; for instance, sensors may be distracting under circumstances where sleep is more difficult, reducing the effectiveness of Pavlovian association, however user may employ system 100 to create the Pavlovian association under ideal sleep circumstances, or on days on which user is especially tired and likely to fall asleep, and then may use kit 300 and/or user-activated scent diffuser 304 to aid in sleeping in more difficult situations. User-activated scent diffuser 304 may require no electricity in an embodiment; as a result, user may be able to carry and use it in situations where electrical power is limited or not present, such as on camping trips or during emergencies or extreme weather events. In addition, the user-activated scent diffuser 304 may enable the user to avoid carrying additional electrical cords, connectors, chargers and electrical plugs including those necessary for use with different international voltages. User-activated scent diffuser 304 may similarly be used in circumstances where electronic devices and/or wireless communication may be restricted, such as airplanes or hospital rooms.

Figure 5:
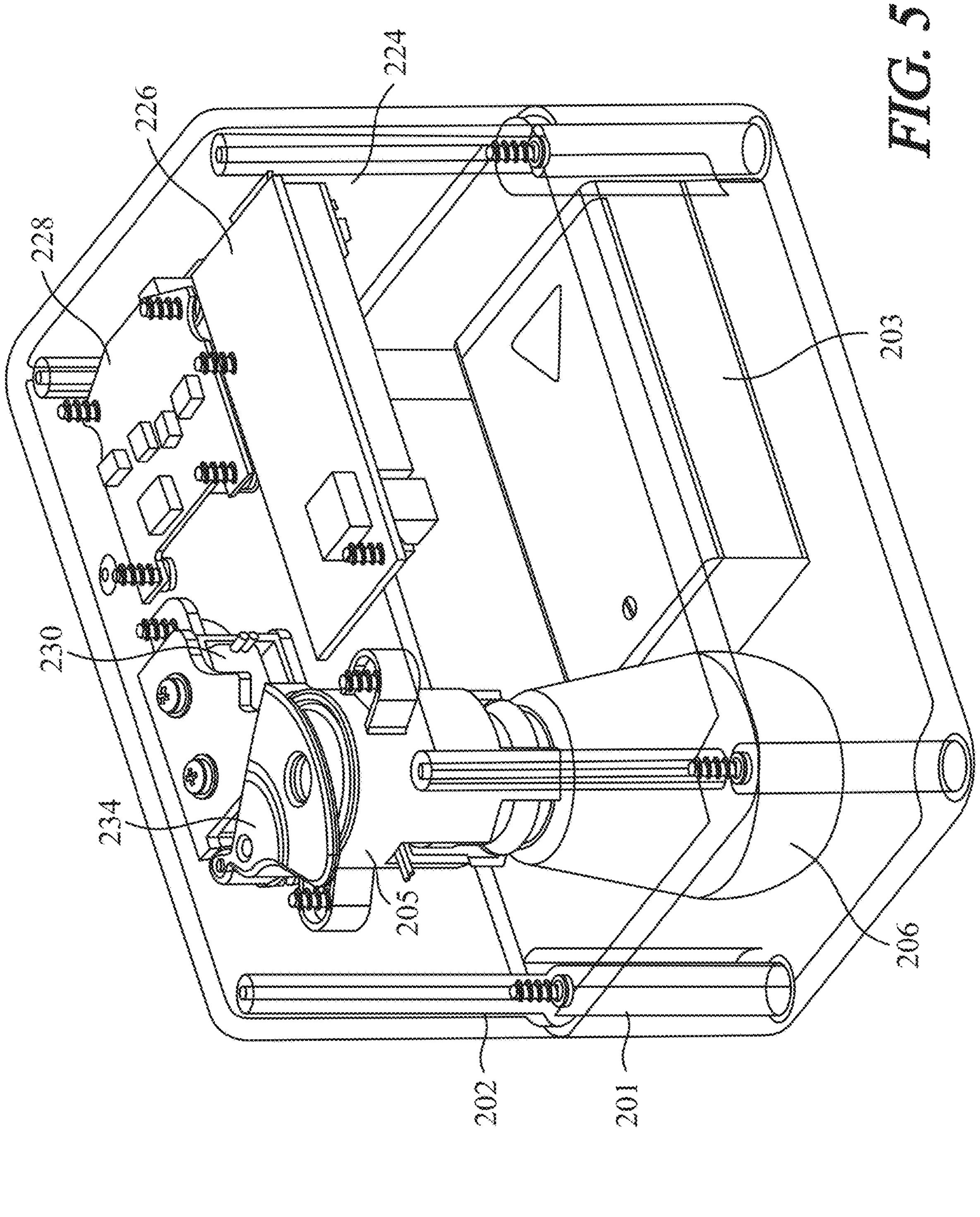
FIG. 5 is a perspective view of an exemplary embodiment of an automatically activated scent diffuser.

FIG. 5 illustrates another embodiment of the automatically activated scent diffuser 108. The system preferably comprises a generally rectangular lower housing portion 201 which includes a compartment 203 for standard alkaline batteries such as size AA batteries, and an upper housing portion 202 which encloses circuitry and a mounting collar or bottle holder 205 for receiving a generally cylindrical bottle 206 adapted to contain a fragrance fluid. Preferably, a lower peripheral rim 222 of the upper housing portion 202 mates with an upper peripheral rim 221 of the lower housing portion 201, and the two housing portions are secured together by screws, threaded through horizontal flanges 209 formed at respective corners of the peripheral rims. It will be apparent that alternative securing structures can be substituted for the screws, by those having ordinary skill in the art.

The circuitry mounted in the upper housing portion 202 suitably comprises a voltage regulator 224 (e.g. model D24V10F5 available from Pololu Corp of Las Vegas NV, USA), a communications module, for example a BLUETOOTH transceiver 226 (such as SparkFun model nRF52832, available from SparkFun Electronics of Niwot, CO, USA), an ultrasonic transducer PCB (printed circuit board) 228, a solenoid or linear actuator 230, and a solenoid control circuit 232 (available from Efcom of Rehovot, Israel). As in the case of ultrasonic transducers used in home humidifiers, PCB 228 drives a generally annular ultrasonic transducer arranged at an outlet opening of the bottle 205 of fragrance fluid; the transducer serves to nebulize the fluid, in order to emit the fragrance into the ambient air surrounding the user of the diffuser. Also mounted in upper housing portion 202 is the bottle holder 205 for receiving the bottle 206 of fragrance fluid. On top of the bottle holder, there is pivotably secured a horizontally oriented shutter 234, formed with a vertical bore or hole 236. Horizontally oriented shutter 234 is mounted at a corner thereof for rotation on a vertically aligned solenoid pin 237, so that shutter 234 can be rotated, for example about 90 degrees, alternately in a first rotation direction and in a second rotation direction. The solenoid 230 is mechanically coupled to the shutter 234, so that the shutter serves as a valve, opening the bottle when the hole 236 in the shutter is aligned with a central opening 246 at the top of the bottle, and closing the bottle when the hole 236 has been pivoted sideways, out of alignment with the bottle central opening 246. Alternatively, the shutter can be pivoted by an electric servo motor (such as model FS90, available from FeeTech RC Model Co. Ltd. of Shenzhen China).

Figure 6:
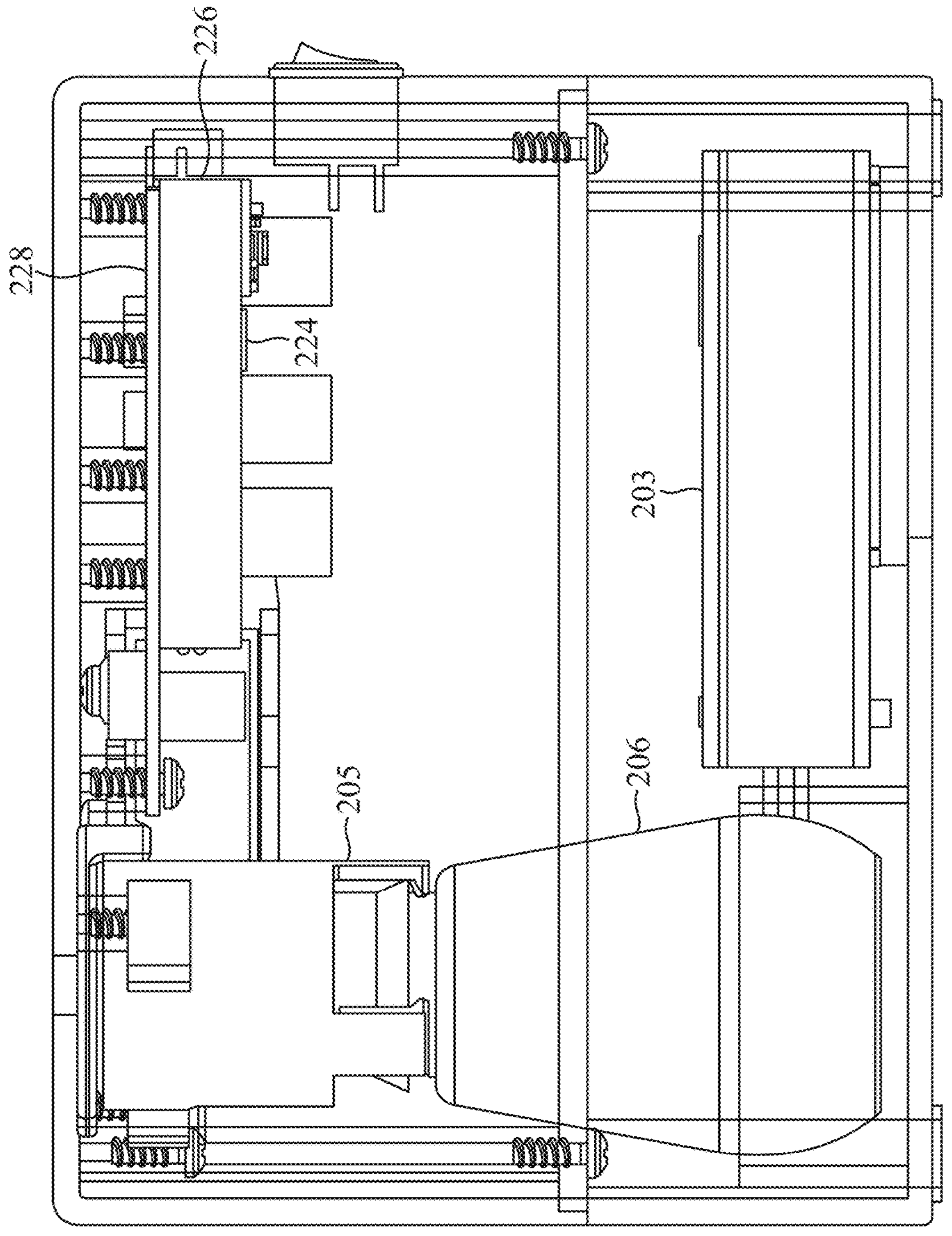
FIG. 6 is a side view, partly in cross section, of the diffuser of FIG. 5.

FIG. 6 is a side view of the diffuser, showing the housing portions in phantom, in order to show an exemplary configuration of the bottle 205, the bottle holder 206 and the respective circuit boards.

Figure 7B:
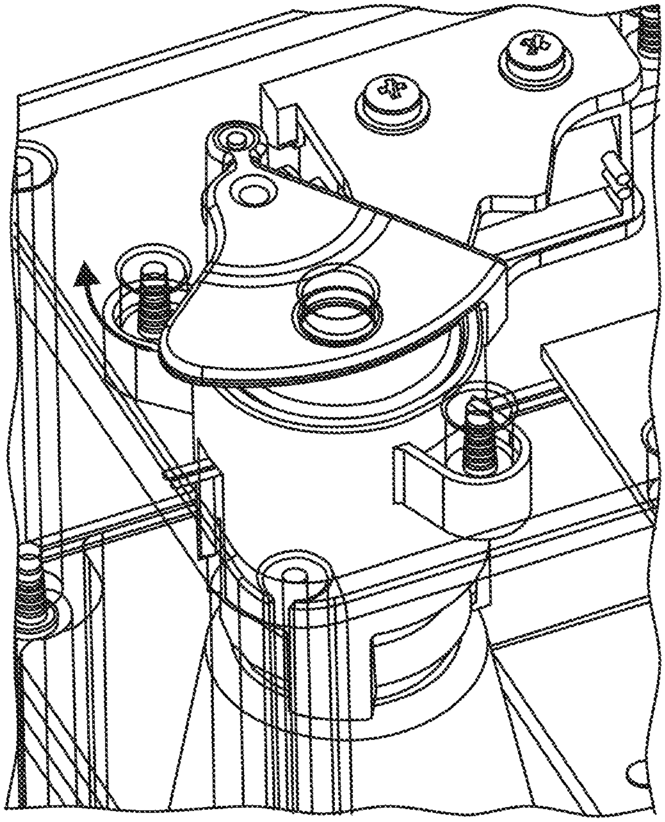
FIGS. 7A & 7B illustrate a bottle-open configuration of the diffuser of FIG. 5.
Figure 7A:
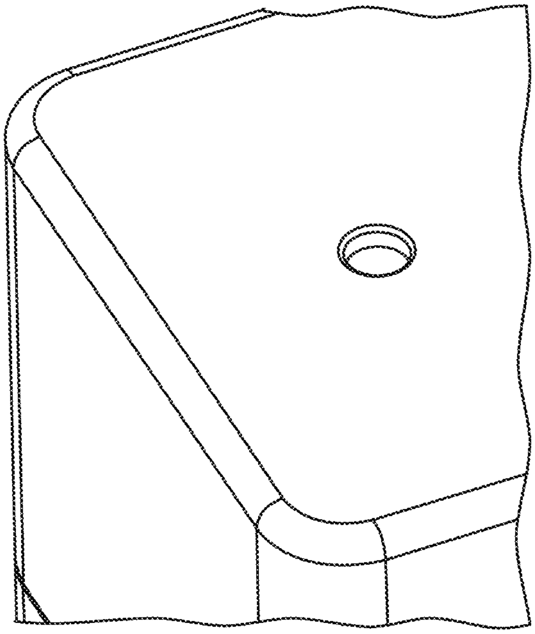
Figure 8B:
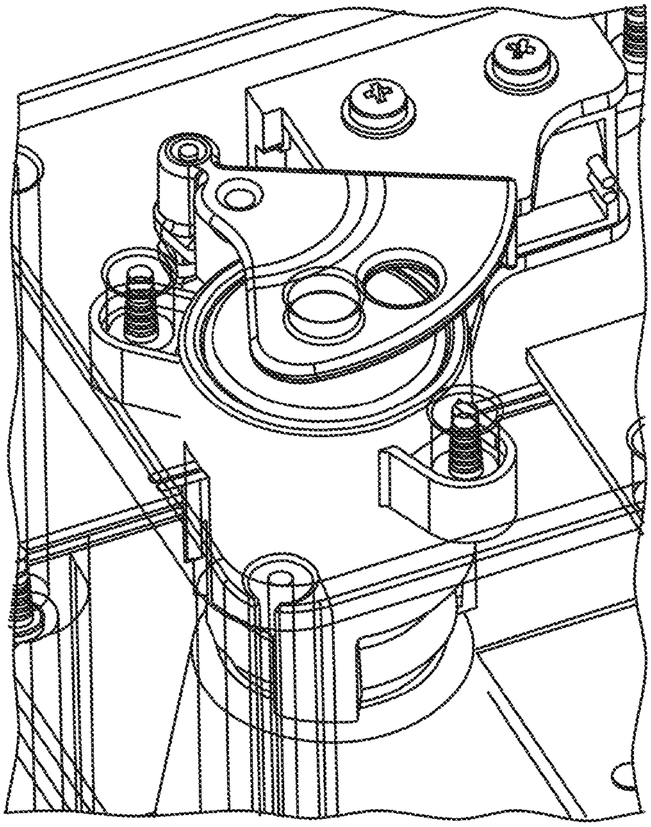
FIGS. 8A & 8B illustrate a bottle-closed configuration of the diffuser of FIG. 5.
Figure 8A:
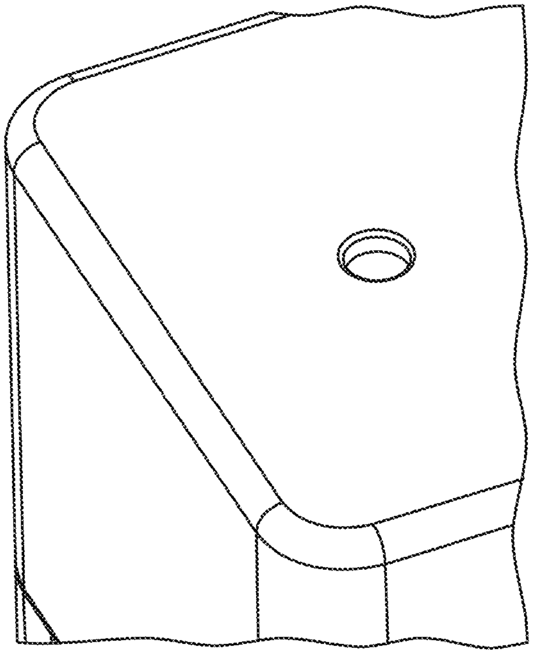

FIGS. 7A and 7B show, respectively, the diffuser exterior and the diffuser interior when the shutter 234 is aligned to open the bottle 205. FIGS. 8A and 8B show, respectively, the diffuser exterior and diffuser interior when shutter 234 is aligned to close bottle 205 by presenting a solid portion of shutter 234 to the central opening 246 of bottle 205. For example, as shown in FIG. 7B, shutter 234 can have a generally triangular shape with a pivot point at one vertex, subtending an angle of 60 degrees. Hole 236 can be formed near an edge of the triangle, remote from the pivot point. Rotating shutter 234 by 20 degrees or so, for example counterclockwise (viewed from above as in FIG. 8B) brings hole 236 out of alignment with opening 246 of bottle 205, thereby bringing a solid portion of shutter 234 adjacent to opening 246, and closing bottle 205.

Figure 9A:
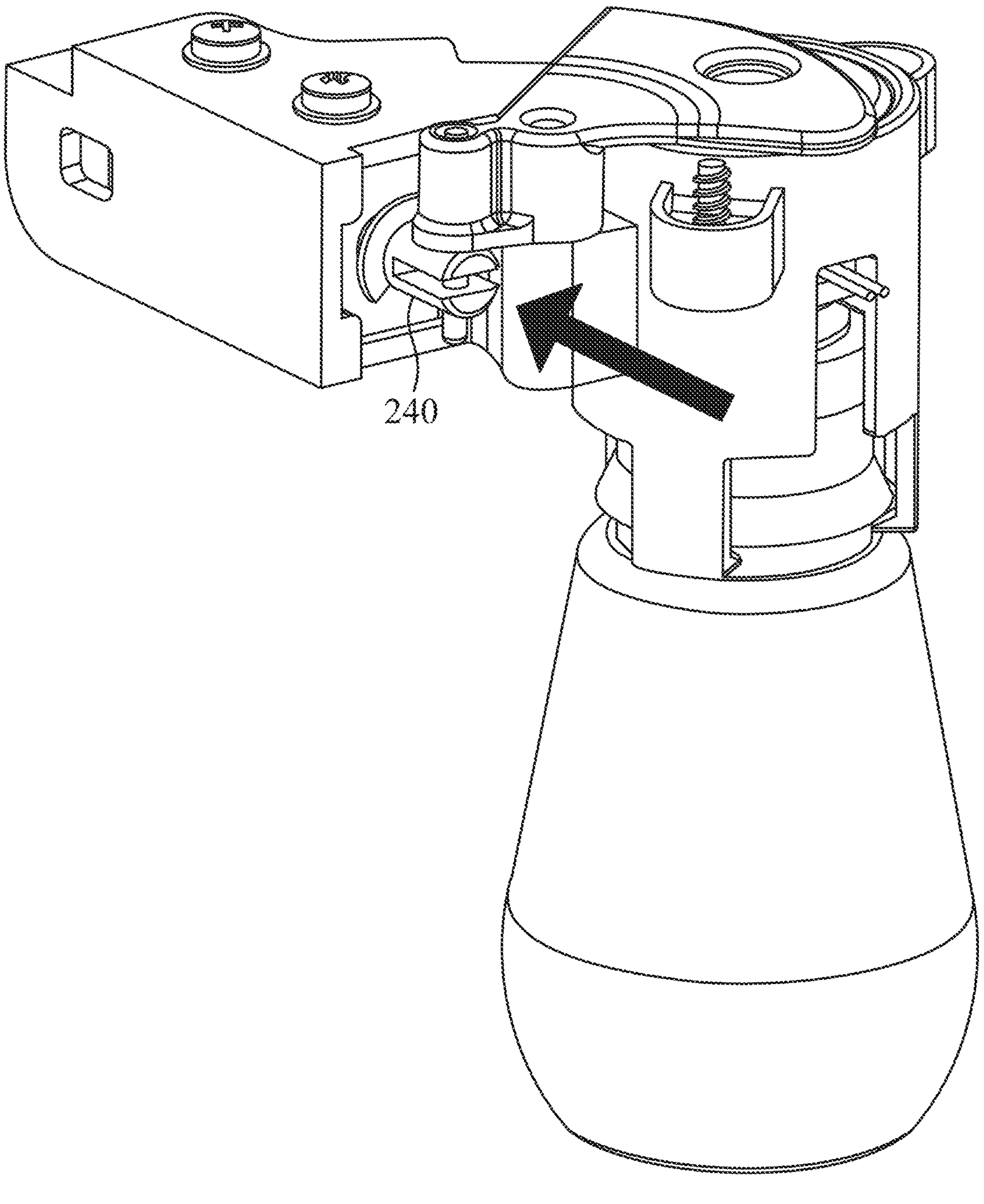
FIG. 9A illustrates a piston-retraction movement of a solenoid in the diffuser of FIG. 5.
Figure 9B:
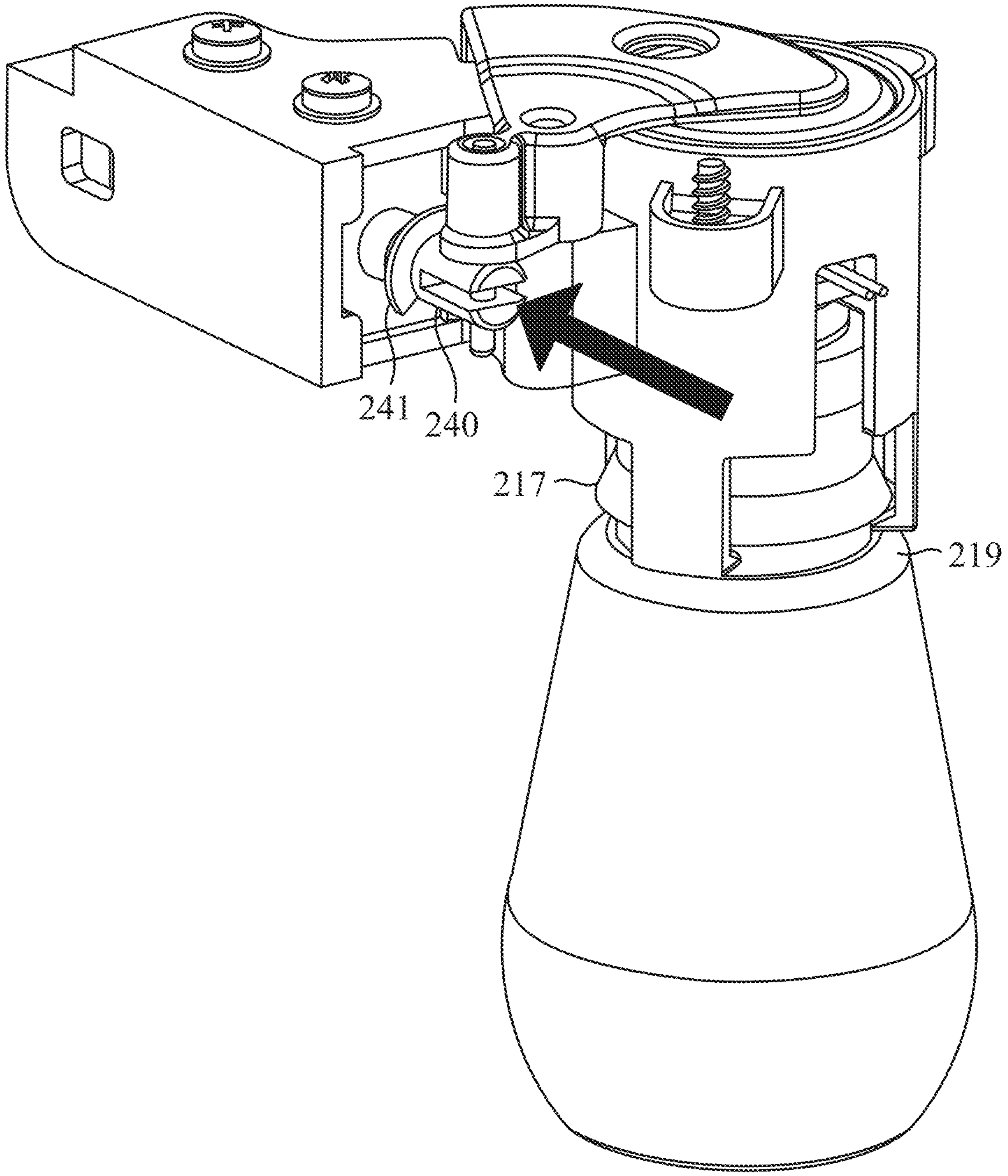
FIG. 9B illustrates a piston-extension stroke or movement of the solenoid.

FIG. 9A and FIG. 9B respectively show how solenoid 230 actuates shutter 234 to switch between a first, bottle-open, configuration and a second, bottle-closed, configuration. A coupling between solenoid 230 and shutter 234 includes a vertically aligned central pin 239 and a vertically aligned solenoid pin 237. The pins are each received within a respective cylindrical sleeve, and the sleeves are rigidly connected to each other by a horizontal bridge 238. A lower end of solenoid pin 237 is received in a vertical bore formed in solenoid piston or plunger 240. Energizing the coil within solenoid 230 retracts piston 240, causing it to exert a pulling force as shown by the arrow in FIG. 9A. An annular stop 241 on the exterior of piston 240 limits the distance that the piston can travel, because stop 241 comes into abutment with an end face of solenoid 230, as may be seen by comparing FIG. 9B (extended) with FIG. 9A (retracted). Central pin 239 is fixed in a portion of bottle holder 205, so bridge 238 causes the sleeve around pin 239 to rotate, and shutter 234 rotates clockwise until shutter hole 236 is vertically aligned with bottle opening 246, allowing scented fluid to be released from the bottle. Conversely, when solenoid 230 is de-energized, piston 240 moves outwardly with respect to solenoid 230, as shown by the arrow in FIG. 9B, and bridge 238 transmits this motion to the sleeve surrounding central pin 239, causing shutter 234 to rotate counter-clockwise, thereby closing bottle 206 and stopping release of scented fluid. Bottle 206 is preferably somewhat tapered, larger in diameter near the bottom, and formed near its top with a radially projecting annular collar 217, beneath which is an annular groove or recess 219, to facilitate secure gripping by bottle holder 205.

Figure 10A:
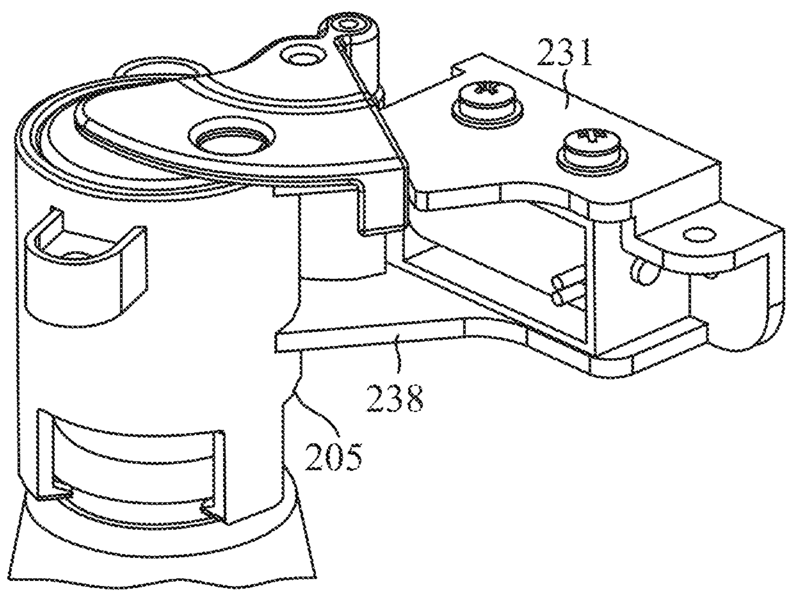
FIGS. 10A & 10B illustrate, from opposing directions, mechanical connections between the solenoid of FIGS. 9A & 9B, and a bottle holder portion of the diffuser of FIG. 5.
Figure 10B:
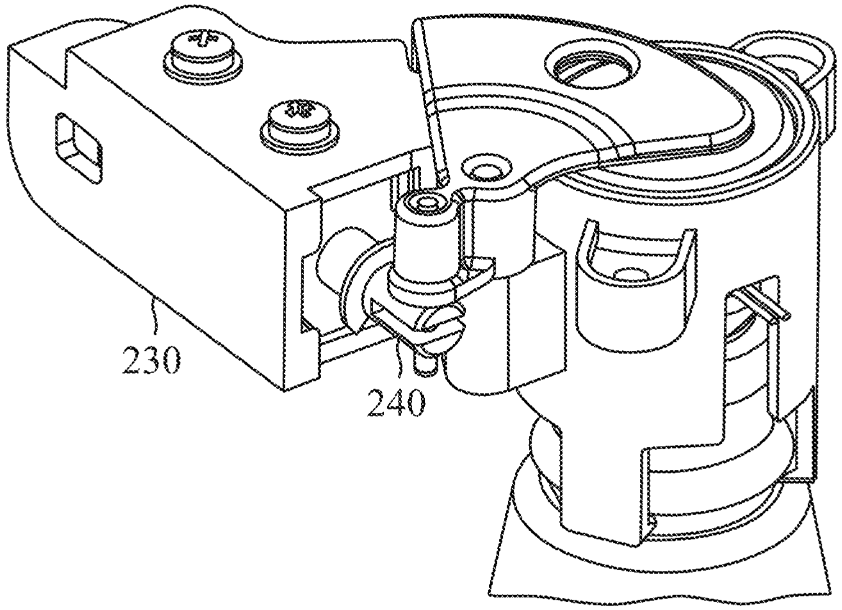

FIG. 10A is a slightly enlarged view similar to FIG. 9B, showing a flat vertical side face of solenoid 230, adapted for fastening to a vertical sidewall in the diffuser. FIG. 10B is a view of the same structure, rotated 180 degrees, to show mechanical connections between bottle holder 205 and solenoid 230.

Figure 11:
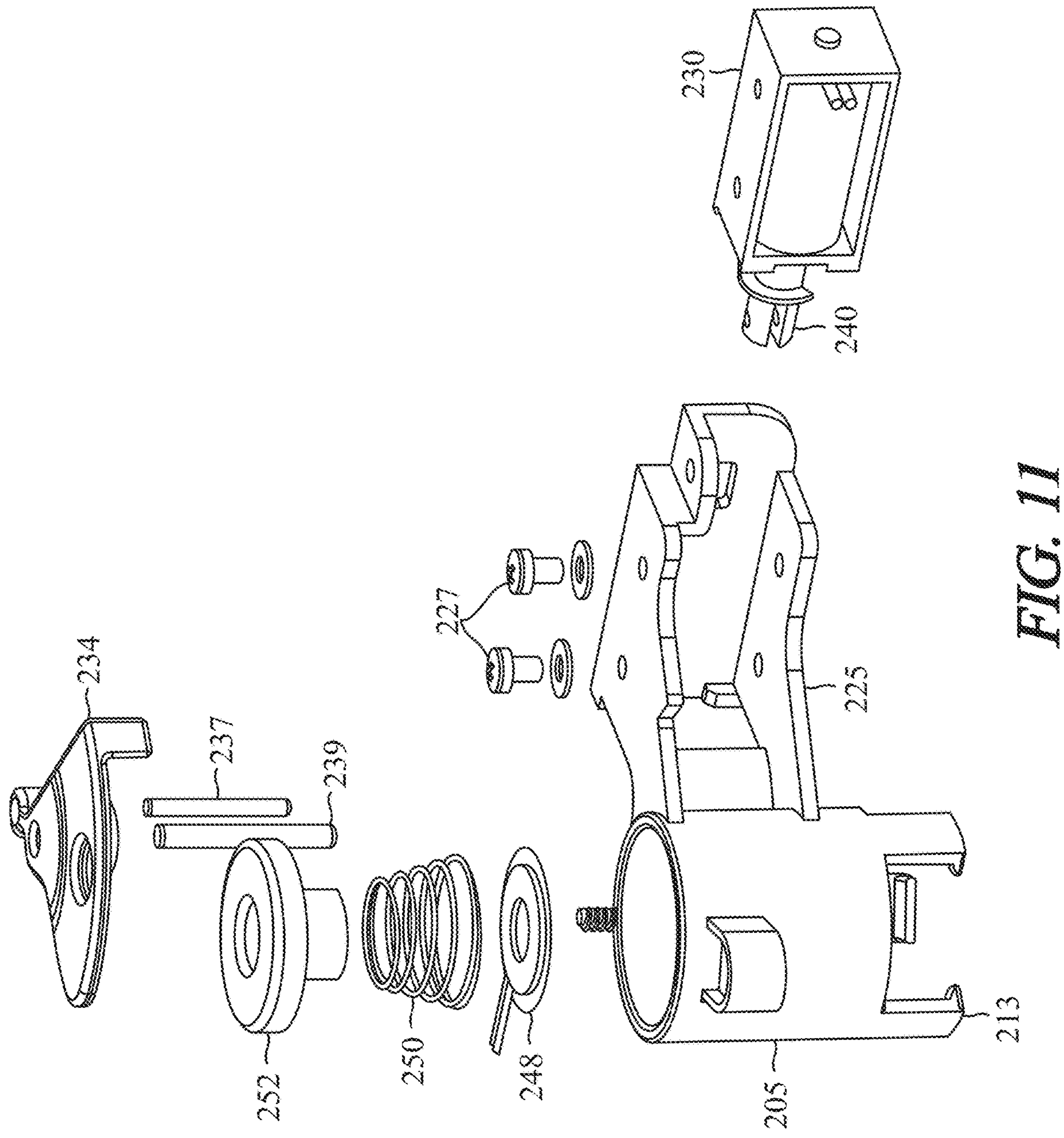
FIG. 11 is an exploded view, showing components of the bottle holder and solenoid portions of the diffuser of FIG. 5.

FIG. 11 is an exploded view, showing components which are assembled to couple bottle holder 205 and solenoid 230 together 0nd to perform fragrance release functions. Bottle holder 205 is preferably a molded plastic element, forming a hollow vertical cylinder with a plurality of depending latches or claws 213 which in vertical cross-section are L-shaped, for example three claws spaced at 120 degree circumferential intervals. The claws point radially inward and are radially resilient, so that a bottle 206 can be inserted axially upwardly into holder 205, and the claws will bow outward momentarily, slide across collar 217 of the bottle, and snap-fit into annular groove 219, thereby holding bottle 206 securely, even if the entire diffuser structure is subsequently vibrated or moved from place to place.

Holder 205 is preferably formed with a laterally projecting U-shaped channel 225 adapted to secure solenoid 230 within it. As shown, channel 225 preferably has a horizontal top wall, a horizontal bottom wall, and a connecting vertical sidewall which interconnects the top & bottom walls, at wall edges remote from the hollow cylindrical portion. Channel 225 is dimensioned to snugly receive solenoid 230 between its top & bottom walls, and against its sidewall. Preferably, respective holes are formed in the top wall and in a top wall of solenoid 230, so that a pair of screws 227 can be inserted through the top wall and into solenoid 230, to thereby secure solenoid 230 within channel 225.

In order to facilitate evaporation and dispersion of scented fluid from bottle 206, a generally disk-shaped ultrasonic transducer 248 is provided, dimensioned to be received within holder 205. Such ultrasonic transducers are widely used in residential humidifying devices, and suitable models are well known to those having ordinary skill in the air treatment and fragrance dispensing arts. As previously mentioned, the transducer is suitably driven by a transducer driving circuit board 228. Optionally, a fan can be provided to help disperse scent droplets produced by the ultrasonic transducer. A coil spring 250 is placed on top of transducer 248. A leading tube 252 with a top annular flange is placed on top of spring 250, so that spring 250 can urge leading tube 252 upward toward shutter 234. This tends to minimize leakage of volatile components of the fragrance fluid from bottle 206 at times when dispensing is not intended. As previously mentioned, a central pin 239 rides within a cylindrical sleeve which is secured to a bottom surface of shutter 234, and a solenoid pin 237 rides within another cylindrical sleeve connected by a bridge 238 to the central pin's sleeve.

Figure 12:
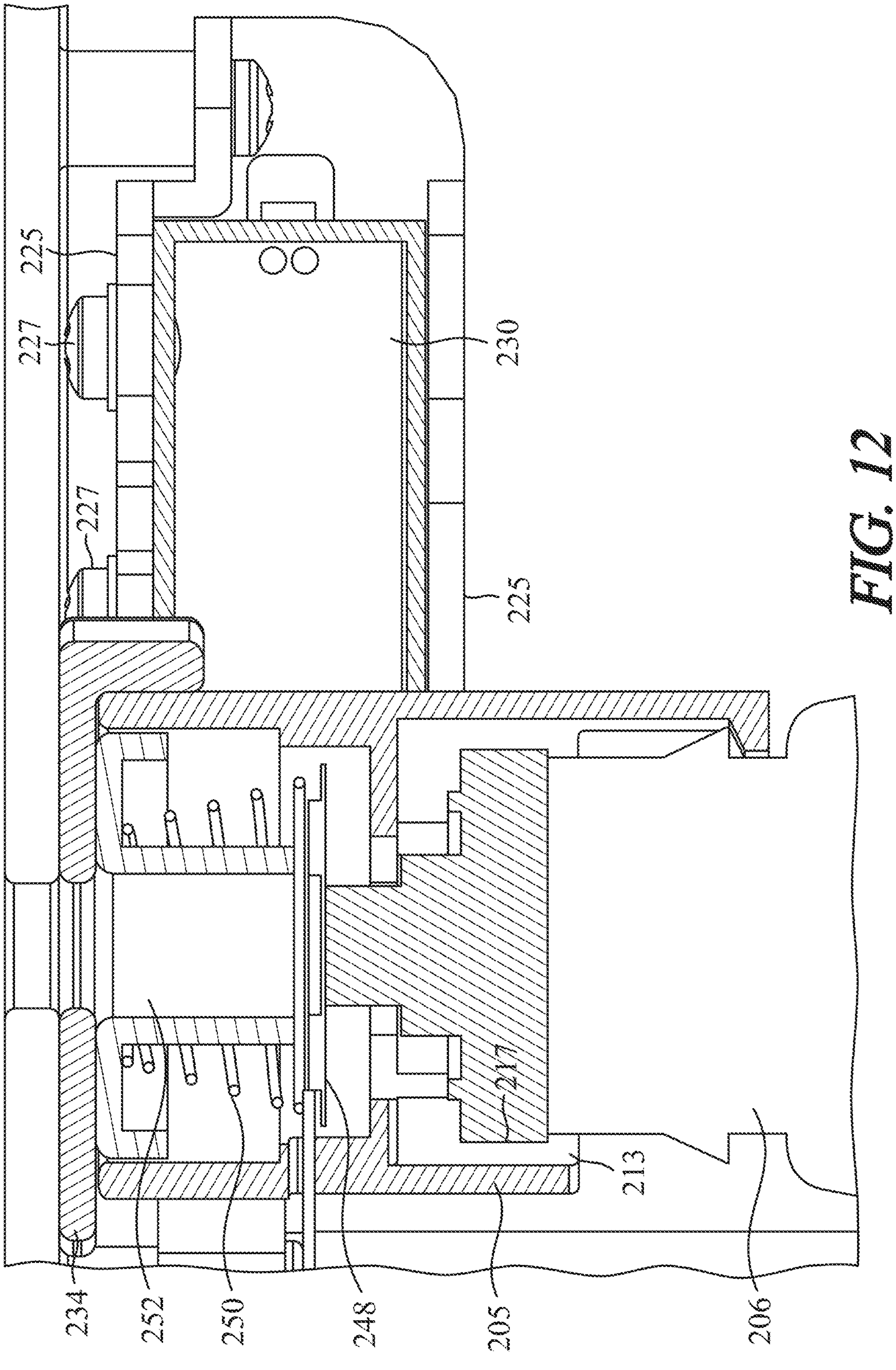
FIG. 12 is a schematic view, partly in cross section, showing an assembled state of the diffuser components of FIG. 11.

FIG. 12 is a view, partly in cross-section, showing the components of FIG. 11 in an assembled state, ready for operation.

Sleep scientists recognize nine sequential electroencephalographic (EEG) stages of sleep. See Tanaka et al., Statistical Features of Hypnagogic EEC Measured by a New Scoring System, published 1976 in the academic journal Sleep, 19(9): 731-738. Preferred methods of "scoring," or distinguishing between, sleep stages have been defined by the American Academy of Sleep Medicine (AASM), presently located in Darien, Illinois, USA.

According to a first embodiment of the conditioning method of the present invention, using electroencephalogram (EEG) sensors, the user applies EEG electrodes to the head, and lies down to go to sleep. Signals from the EEG electrodes are fed to a computing device, for example to a smart mobile phone running the Apple operating system iOS or the Android operating system. Upon detection of EEG stage 1 (continuous train of alpha waves having a minimum amplitude of 20 microvolts), an electronic activation signal is sent, for example using the BLUETOOTH communications protocol or the ANT+ protocol of Garmin Canada, to automatic scent diffuser 108, causing solenoid 230 to place shutter 234 in a bottle-open configuration (FIGS. 7A, 9A) and causing transducer circuit 228 to operate transducer 248 to nebulize fragrance fluid coming from bottle 206. Optionally, faster diffusion can be obtained by turning on a small fan (not shown) adjacent to transducer 248. The diffusion of fragrance continues as the user progresses into EEG stages 2 and 3. Typically, a user will be in stage 2 (alpha waves intermittent but still present for more than 50% of a sampling period) for about three and one half minutes. Upon detection of a beginning of sleep stage 3 (alpha waves intermittent but now present for less than 50% of a sampling period), a countdown timer is set for generation of a deactivation signal to the automatic scent diffuser. As in the case of the activation signal, the deactivation signal is preferably sent via BLUETOOTH or ANT+. Preferably, the countdown timer is set to generate the deactivation signal a predetermined period, e.g. 30 seconds, after the start of sleep stage 3. Alternatively, the duration of the predetermined period can be selected by consulting a lookup table, which associates a particular predetermined characteristic of the user with a respective duration. Upon receipt by diffuser 108 of the deactivation signal, ultrasonic transducer is turned off and solenoid 230 closes shutter 234 (FIG. 9B), stopping release of fragrance fluid. Since the user is now in a state less susceptible to perception of the fragrance (and thus association of fragrance with sleep), cessation of fragrance emission tends to conserve fragrance fluid until a subsequent falling-asleep session. Preferably, if the user spontaneously awakens during the same night, a new conditioning session is performed. Preferably, at least one conditioning session is conducted on each of a plurality of successive days. Thereby, the user becomes conditioned to relax and fall asleep, each time the fragrance is perceived. Scholars Fujiwara et al., in an article entitled Heart Rate Variability-Based Driver Drowsiness Detection and its Validation with EEG, IEEE Transactions on Biomedical Engineering, Vol. 66, No. 6, pages 1769-1778, June 2019, disclose a suitable program for processing EEG sensor data to detect transitions between sleep states.

According to a second embodiment of the method of the invention, using electrocardiogram (ECG) sensors, the AASM (American Academy of Sleep Medicine) sleep states (wake, Rapid Eye Movement (REM) sleep, and 3 levels of non-REM sleep: NREM1, NREM2, NREM3) are distinguished, using signals from a commercially available fitness sensor, such as the POLAR model H10 which is typically sold with a chest strap. The model H10 is currently available from Polar Electro Inc., located at 15 Grumman Road West, Suite 1200, Bethpage, NY 11714, USA. Other suitable sensors are known to those having ordinary skill in the sleep-stage monitoring art. For simplicity, the non-REM states NREM1, NREM2 and NREM3 are also referred to as "N1, N2, N3." The so-called "RR" intervals between heartbeats are very accurately detected by capturing the signals from the wearable ECG sensors, in order to analyze Heart Rate Variability (HRV). HRV and related parameters (preferably blood pressure and blood vessel size) are processed, to detect physiological changes in the sensor wearer, corresponding to an early N1 sleep state. Detection of that HRV pattern causes activation of the bedside automatic scent diffuser (by a signal sent from a suitable app running on a smart phone, linked to the sensor using the BLUETOOTH protocol or the ANT+ protocol). The activation is maintained for a period of 10 minutes, corresponding to the early N1 state. When 10 minutes has elapsed since sending of the activation signal, a deactivation signal is sent from the app running on the smart phone. For example, the Polar Electro company of Bethpage NY offers a smartphone app under the mark BEAT (US Reg. #2,034,443). Suitable sensor structures are disclosed in one or more of Polar Electro's U.S. Pat. Nos. 10,064,581; 10,070,798; 10,146,297; 10,154,129; 10,313,420; 10,314,506; 10,335,636 and US published application 2019-0254524. Automated sleep stage classification using heart rate variability is described in the 12 Sep. 2018 article of Radha et al., entitled LSTM Knowledge Transfer for HRV-based Sleep Staging, arXiv: 1809.06221v1.

Figure 13:
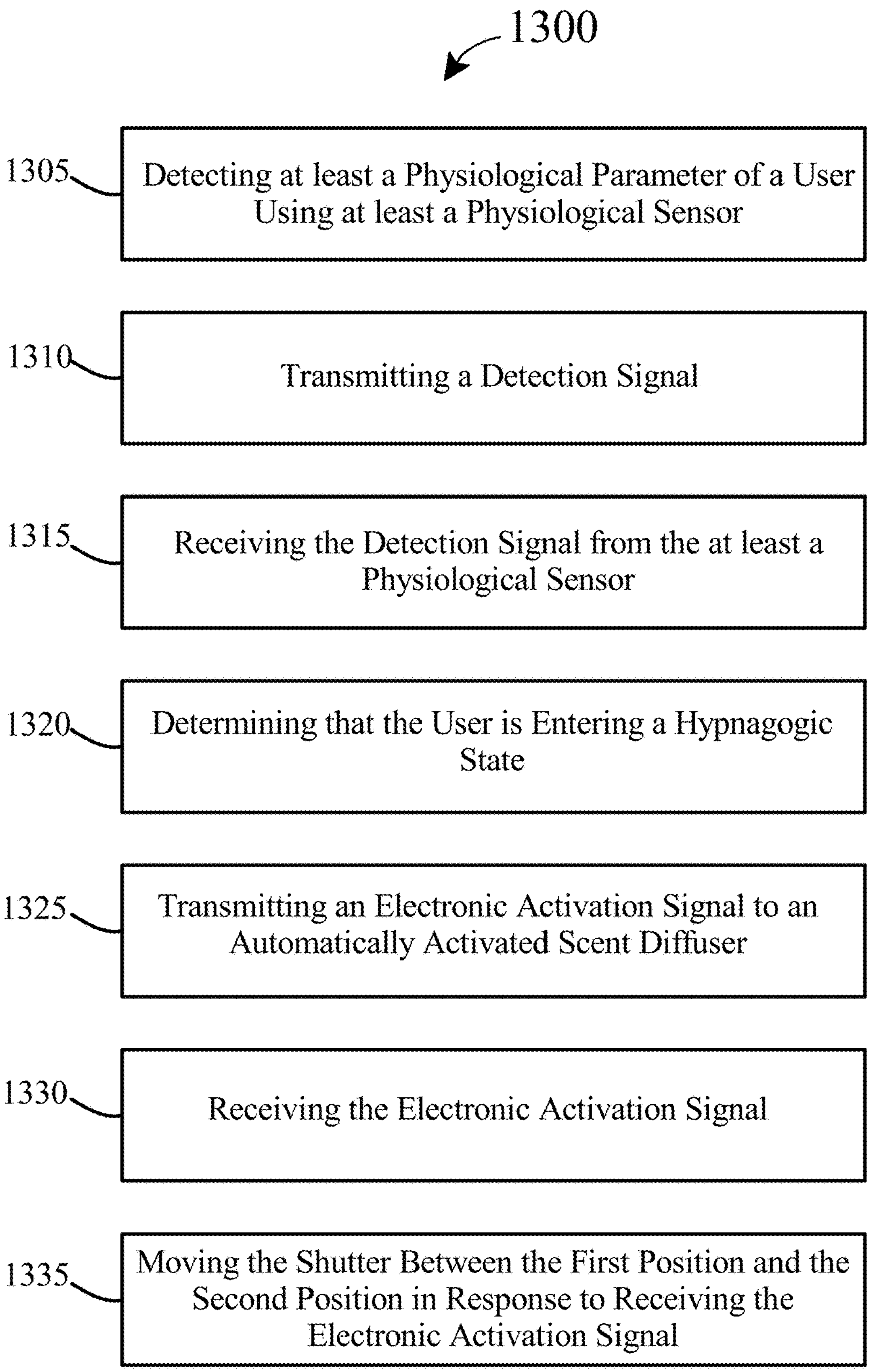
FIG. 13 is a flow diagram of an exemplary embodiment of a method for inducing a Pavlovian conditioned reflex association of a scent with sleep initiation.

Referring now to FIG. 13, an exemplary embodiment of a method 1300 for inducing a Pavlovian conditioned reflex association of a scent with sleep initiation is shown. Method 1300 includes a step 1305 of detecting at least a physiological parameter of a user using at least a physiological sensor. This may be implemented as disclosed with reference to FIGS. 1-12 above.

With continued reference to FIG. 13, method 1300 includes a step 1310 of transmitting, by the physiological sensor, a detection signal. This may be implemented as disclosed with reference to FIGS. 1-12 above.

With continued reference to FIG. 13, method 1300 includes a step 1315 of receiving, by a control circuit, the detection signal from the at least a physiological sensor. This may be implemented as disclosed with reference to FIGS. 1-12 above.

With continued reference to FIG. 13, method 1300 includes a step 1320 of determining, by the control circuit, that the user is entering a hypnagogic state. This may be implemented as disclosed with reference to FIGS. 1-12 above. In some embodiments, step 1320 may further include determining that the detected at least a physiological parameter indicates a state of pre-sleep relaxation. This may be implemented as disclosed with reference to FIGS. 1-12 above. In some embodiments, step 1320 may further include determining using a linear regression machine-learning model, a pattern associated with the detected at least a physiological parameter. This may be implemented as disclosed with reference to FIGS. 1-12 above. In some embodiments, step 1320 may further include calculating an average time from detection of indication of pre-sleep relaxation to detection of entry into a hypnagogic state associated with the user as a function of the pattern. This may be implemented as disclosed with reference to FIGS. 1-12 above. In some embodiments, step 1320 may further include predicting a user's time of entry into a hypnagogic state based on the average time. This may be implemented as disclosed with reference to FIGS. 1-12 above. In some embodiments, step 1320 may further include determining the user's entry into a hypnagogic state is imminent at a time point between the indication of pre-sleep relaxation and the predicted time of entry into a hypnagogic state. This may be implemented as disclosed with reference to FIGS. 1-12 above.

With continued reference to FIG. 13, method 1300 includes a step 1325 of transmitting, by the control circuit, an electronic activation signal to an automatically activated scent diffuser. This may be implemented as disclosed with reference to FIGS. 1-12 above.

With continued reference to FIG. 13, method 1300 includes a step 1330 of receiving, by the automatically activated scent diffuser, the electronic activation signal. This may be implemented as disclosed with reference to FIGS. 1-12 above. The automatically activated scent diffuser includes a housing, the housing including a compartment, wherein the compartment including a scent-diffusing material. The automatically activated scent diffuser further includes diffusing vent aperture disposed on the housing, wherein the diffusing vent aperture is in communication with the compartment. The automatically activated scent diffuser further includes shutter rotatably mounted to housing, wherein the shutter has a first position wherein the shutter opens the diffusing vent aperture, and the shutter has a second position wherein the shutter closes the diffusing vent aperture. The automatically activated scent diffuser further includes a linear actuator. The shutter may be consistent with any shutter disclosed in this disclosure. The automatically actuated scent diffuser may be consistent with any automatically actuated scent diffuser disclosed in this disclosure. In some embodiments, the automatically activated scent diffuser may further include a transducer in communication with the diffusing vent aperture. In some embodiments, the linear actuator may be a solenoid. In some embodiments, the automatically activated scent diffuser may further include a central pin wherein the central pin is fixed to the housing; and the shutter is rotatably connected to the central pin. In some embodiments, the automatically activated scent diffuser may further include a solenoid pin, wherein the solenoid pin is connected to the shutter and the linear actuator. In some embodiments, the shutter may comprise a solid portion, wherein the solid portion defines a hole. In some embodiments, when the shutter is in the first position, the hole is located on top of the diffusing vent aperture. In some embodiments, when the shutter is in the second position, the solid portion is located on top of the diffusing vent aperture. In some embodiments, the automatically activated scent diffuser may further include a fan. In some embodiments, the container may be a bottle. In some embodiments, the bottle may include a collar. In some embodiments, the bottle may include an adjacent groove. The bottle may be consistent with any bottle disclosed as part of this disclosure. In some embodiments, the automatically activated scent diffuser may further include a holder, wherein the holder is attached to the linear actuator and the container and configured to receive the bottle. In some embodiments, the holder may include a plurality of claws, wherein the claws point radially inward and are configured to snap-fit into the adjacent groove of the bottle.

With continued reference to FIG. 13, method 1300 includes a step 1335 of moving the shutter, by the linear actuator, between the first position and the second position in response to receiving the electronic activation signal. This may be implemented as disclosed with reference to FIGS. 1-12 above. In some embodiments, step 1335 may further include displacing, by the linear actuator, the solenoid pin. This may be implemented as disclosed with reference to FIGS. 1-12 above.

Figure 14:
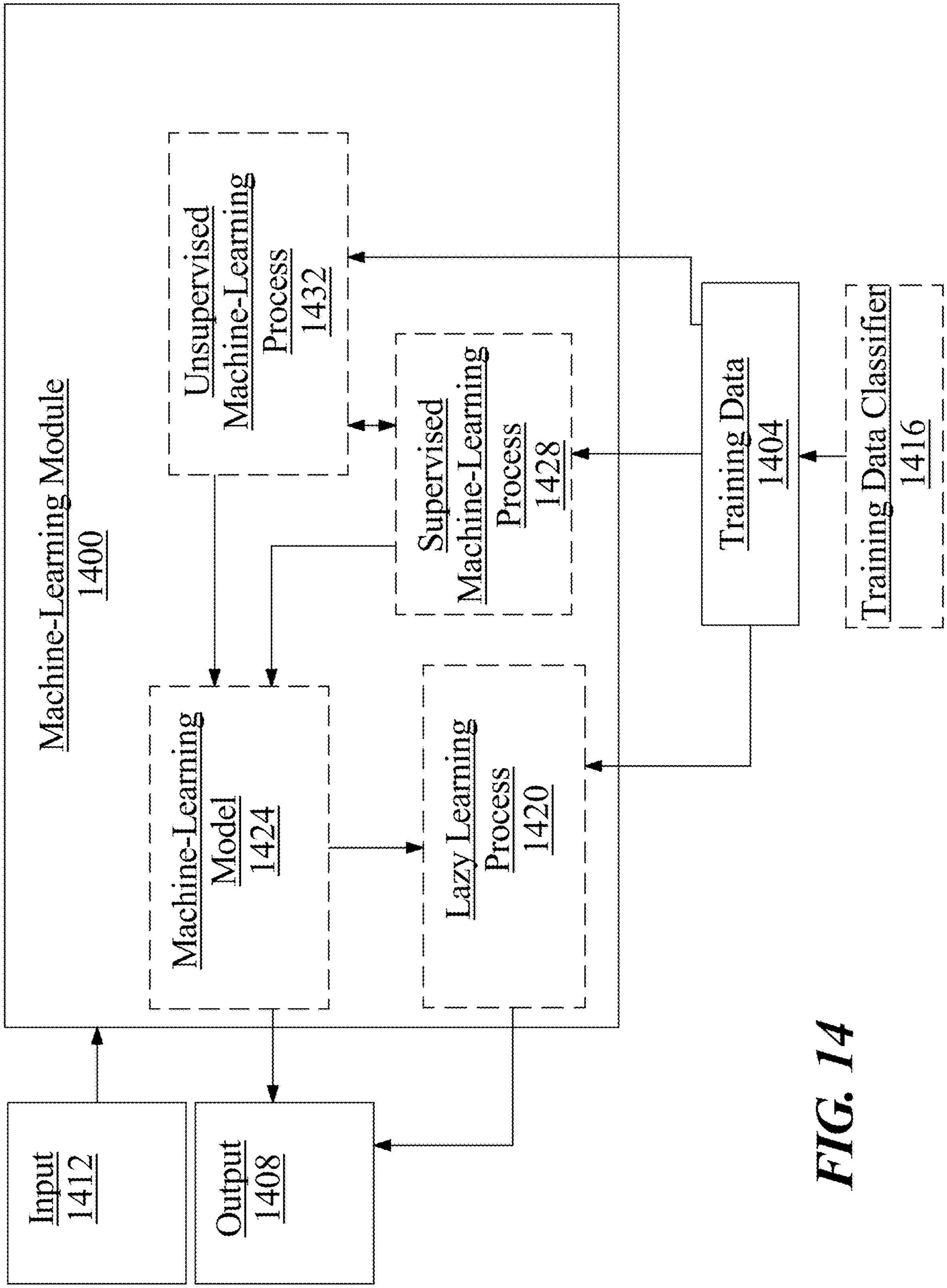
FIG. 14 is a block diagram of an exemplary machine-learning module.

Referring now to FIG. 14, an exemplary embodiment of a machine-learning module 1400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 1404 to generate an algorithm that will be performed by a computing device/module to produce outputs 1408 given data provided as inputs 1412; this is in contrast to a non-machine learning software program where the commands to be executed are determined in advance by a user and written in a programming language.

Still referring to FIG. 14, "training data," as used herein, is data containing correlations that a machine-learning process may use to model relationships between two or more categories of data elements. For instance, and without limitation, training data 1404 may include a plurality of data entries, each entry representing a set of data elements that were recorded, received, and/or generated together; data elements may be correlated by shared existence in a given data entry, by proximity in a given data entry, or the like. Multiple data entries in training data 1404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 1404 according to various correlations; correlations may indicate causative and/or predictive links between categories of data elements, which may be modeled as relationships such as mathematical relationships by machine-learning processes as described in further detail below. Training data 1404 may be formatted and/or organized by categories of data elements, for instance by associating data elements with one or more descriptors corresponding to categories of data elements. As a non-limiting example, training data 1404 may include data entered in standardized forms by persons or processes, such that entry of a given data element in a given field in a form may be mapped to one or more descriptors of categories. Elements in training data 1404 may be linked to descriptors of categories by tags, tokens, or other data elements; for instance, and without limitation, training data 1404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 14, training data 1404 may include one or more elements that are not categorized; that is, training data 1404 may not be formatted or contain descriptors for some elements of data. Machine-learning algorithms and/or other processes may sort training data 1404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 1404 to be made applicable for two or more distinct machine-learning algorithms as described in further detail below. Training data 1404 used by machine-learning module 1400 may correlate any input data as described in this disclosure to any output data as described in this disclosure.

Further referring to FIG. 14, training data may be filtered, sorted, and/or selected using one or more supervised and/or unsupervised machine-learning processes and/or models as described in further detail below; such models may include without limitation a training data classifier 1416. Training data classifier 1416 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 1400 may generate a classifier using a classification algorithm, defined as a processes whereby a computing device and/or any module and/or component operating thereon derives a classifier from training data 1404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 14, machine-learning module 1400 may be configured to perform a lazy-learning process 1420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 1404. Heuristic may include selecting some number of highest-ranking associations and/or training data 1404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 14, machine-learning processes as described in this disclosure may be used to generate machine-learning models 1424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 1424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 1424 may be generated by creating an artificial neural network, such as a convolutional neural network comprising an input layer of nodes, one or more intermediate layers, and an output layer of nodes. Connections between nodes may be created via the process of "training" the network, in which elements from a training data 1404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 14, machine-learning algorithms may include at least a supervised machine-learning process 1428. At least a supervised machine-learning process 1428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs, [outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 1404. Persons skilled in the art, upon reviewing the entirety of this disclosure, will be aware of various possible variations of at least a supervised machine-learning process 1428 that may be used to determine relation between inputs and outputs. Supervised machine-learning processes may include classification algorithms as defined above.

Further referring to FIG. 14, machine learning processes may include at least an unsupervised machine-learning processes 1432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 14, machine-learning module 1400 may be designed and configured to create a machine-learning model 1424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 14, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 15:
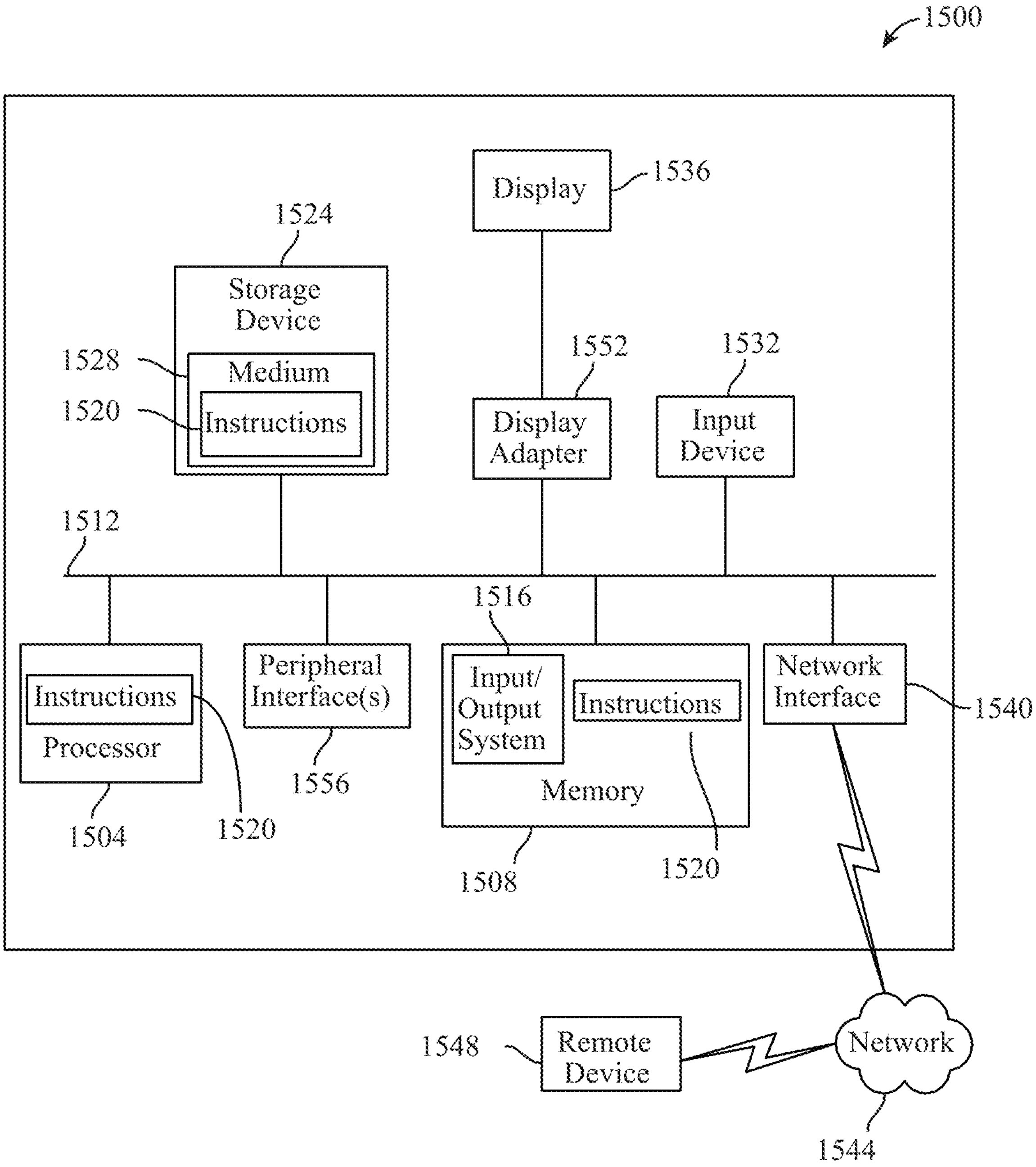
FIG. 15 is a block diagram of a computing system that can be used to implement any one or more of the methodologies disclosed herein and any one or more portions thereof.

FIG. 15 shows a diagrammatic representation of one embodiment of a computing device in the exemplary form of a computer system 1500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1500 includes a processor 1504 and a memory 1508 that communicate with each other, and with other components, via a bus 1512. Bus 1512 may include any of several types of bus structures including, but not limited to, a memory bus, a memory controller, a peripheral bus, a local bus, and any combinations thereof, using any of a variety of bus architectures.

Processor 1504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1504 may be organized according to Von Neumann and/or Harvard architecture as a non-limiting example. Processor 1504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1508 may include various components (e.g., machine-readable media) including, but not limited to, a random-access memory component, a read only component, and any combinations thereof. In one example, a basic input/output system 1516 (BIOS), including basic routines that help to transfer information between elements within computer system 1500, such as during start-up, may be stored in memory 1508. Memory 1508 may also include (e.g., stored on one or more machine-readable media) instructions (e.g., software) 1520 embodying any one or more of the aspects and/or methodologies of the present disclosure. In another example, memory 1508 may further include any number of program modules including, but not limited to, an operating system, one or more application programs, other program modules, program data, and any combinations thereof.

Computer system 1500 may also include a storage device 1524. Examples of a storage device (e.g., storage device 1524) include, but are not limited to, a hard disk drive, a magnetic disk drive, an optical disc drive in combination with an optical medium, a solid-state memory device, and any combinations thereof. Storage device 1524 may be connected to bus 1512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1524 (or one or more components thereof) may be removably interfaced with computer system 1500 (e.g., via an external port connector (not shown)). Particularly, storage device 1524 and an associated machine-readable medium 1528 may provide nonvolatile and/or volatile storage of machine-readable instructions, data structures, program modules, and/or other data for computer system 1500. In one example, software 1520 may reside, completely or partially, within machine-readable medium 1528. In another example, software 1520 may reside, completely or partially, within processor 1504.

Computer system 1500 may also include an input device 1532. In one example, a user of computer system 1500 may enter commands and/or other information into computer system 1500 via input device 1532. Examples of an input device 1532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1532 may be interfaced to bus 1512 via any of a variety of interfaces (not shown) including, but not limited to, a serial interface, a parallel interface, a game port, a USB interface, a FIREWIRE interface, a direct interface to bus 1512, and any combinations thereof. Input device 1532 may include a touch screen interface that may be a part of or separate from display 1536, discussed further below. Input device 1532 may be utilized as a user selection device for selecting one or more graphical representations in a graphical interface as described above.

A user may also input commands and/or other information to computer system 1500 via storage device 1524 (e.g., a removable disk drive, a flash drive, etc.) and/or network interface device 1540. A network interface device, such as network interface device 1540, may be utilized for connecting computer system 1500 to one or more of a variety of networks, such as network 1544, and one or more remote devices 1548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1544, may employ a wired and/or a wireless mode of communication. In general, any network topology may be used. Information (e.g., data, software 1520, etc.) may be communicated to and/or from computer system 1500 via network interface device 1540.

Computer system 1500 may further include a video display adapter 1552 for communicating a displayable image to a display device, such as display device 1536. Examples of a display device include, but are not limited to, a liquid crystal display (LCD), a cathode ray tube (CRT), a plasma display, a light emitting diode (LED) display, and any combinations thereof. Display adapter 1552 and display device 1536 may be utilized in combination with processor 1504 to provide graphical representations of aspects of the present disclosure. In addition to a display device, computer system 1500 may include one or more other peripheral output devices including, but not limited to, an audio speaker, a printer, and any combinations thereof. Such peripheral output devices may be connected to bus 1512 via a peripheral interface 1556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for inducing a Pavlovian conditioned reflex association of a scent with sleep initiation, the system comprising:

at least a physiological sensor, wherein the at least a physiological sensor is configured to detect at least a physiological parameter of a user and to transmit a detection signal;

a control circuit configured to receive the detection signal from the at least a physiological sensor, determine that the user is entering a hypnagogic state, and transmit an electronic activation signal; and an automatically activated scent diffuser, wherein:

the automatically activated scent diffuser is configured to receive the electronic activation signal; and the automatically activated scent diffuser comprises:

a housing, the housing comprising a compartment, wherein the compartment comprises a scent-diffusing material;

a diffusing vent aperture disposed on the housing, wherein the diffusing vent aperture is in communication with the compartment;

a linear actuator; and a shutter rotatably mounted to the housing, wherein:

the shutter has a first position wherein the shutter opens the diffusing vent aperture;

the shutter has a second position wherein the shutter closes the diffusing vent aperture; and the shutter is configured to be moved by the linear actuator between the first position and the second position in response to receiving the electronic activation signal.

2. The system of claim 1, wherein the automatically activated scent diffuser further comprises a transducer in communication with the diffusing vent aperture.

3. The system of claim 1, wherein the linear actuator is a solenoid.

4. The system of claim 1, wherein the automatically activated scent diffuser further comprises a central pin, wherein:

the central pin is fixed to the housing; and the shutter is rotatably connected to the central pin.

5. The system of claim 4, wherein the automatically activated scent diffuser further comprises: a solenoid pin, wherein:

the solenoid pin is connected to the shutter and the linear actuator; and the linear actuator is configured to move the shutter between the first position and the second position by displacing the solenoid pin.

6. The system of claim 1, wherein the automatically activated scent diffuser further comprises a holder, wherein the holder is attached to the linear actuator and is configured to receive a bottle.

7. The system of claim 6, wherein:

the bottle comprises a collar and an adjacent groove; and the holder comprises a plurality of claws, wherein the plurality of claws point radially inward and are configured to snap-fit into the adjacent groove of the bottle.

8. The system of claim 1, wherein the automatically activated scent diffuser further comprises a fan.

9. The system of claim 1, wherein the shutter comprises a solid portion, the solid portion defining a hole, wherein:

when the shutter is in the first position, the hole is located on top of the diffusing vent aperture; and when the shutter is in the second position, the solid portion is located on top of the diffusing vent aperture.

10. The system of claim 1, wherein determining that the user is entering the hypnagogic state comprises:

determining that the detected at least a physiological parameter indicates a state of pre-sleep relaxation;

determining, using a linear regression machine-learning model, a pattern associated with the detected at least a physiological parameter; and calculating an average time from detection of indication of the state of pre-sleep relaxation to detection of entry into the hypnagogic state associated with the user as a function of the pattern.

11. The system of claim 10, wherein determining that the user is entering the hypnagogic state further comprises predicting a user's time of entry into the hypnagogic state based on the average time.

12. The system of claim 11, wherein determining that the user is entering the hypnagogic state further comprises determining the user's entry into a hypnagogic state is imminent at a time point between the indication of the state of pre-sleep relaxation and the predicted user's time of entry into the hypnagogic state.

13. A method for inducing a Pavlovian conditioned reflex association of a scent with sleep initiation, the method comprising:

detecting at least a physiological parameter of a user using at least a physiological sensor;

transmitting, by the at least a physiological sensor, a detection signal;

receiving, by a control circuit, the detection signal from the at least a physiological sensor; determining, by the control circuit, that the user is entering a hypnagogic state;

transmitting, by the control circuit, an electronic activation signal to an automatically activated scent diffuser;

receiving, by the automatically activated scent diffuser, the electronic activation signal, wherein the automatically activated scent diffuser comprises:

a housing, the housing comprising a compartment, wherein the compartment comprises a scent-diffusing material;

a diffusing vent aperture disposed on the housing, wherein the diffusing vent aperture is in communication with the compartment;

a shutter rotatably mounted to the housing, wherein:

the shutter has a first position wherein the shutter opens the diffusing vent aperture;

the shutter has a second position wherein the shutter closes the diffusing vent aperture; and a linear actuator; and moving the shutter, by the linear actuator, between the first position and the second position in response to receiving the electronic activation signal.

14. The method of claim 13, wherein the automatically activated scent diffuser further comprises a transducer in communication with the diffusing vent aperture.

15. The method of claim 13, wherein the linear actuator is a solenoid.

16. The method of claim 13, wherein:

the automatically activated scent diffuser further comprises:

a central pin, wherein:

the central pin is fixed to the housing; and the shutter is rotatably connected to the central pin; and a solenoid pin, wherein the solenoid pin is connected to the shutter and the linear actuator; and moving the shutter between the first position and the second position comprises displacing, by the linear actuator, the solenoid pin.

17. The method of claim 13, wherein the automatically activated scent diffuser further comprises a fan.

18. The method of claim 13, wherein determining that the user is entering the hypnagogic state comprises:

determining that the detected at least a physiological parameter indicates a state of pre-sleep relaxation;

determining using a linear regression machine-learning model, a pattern associated with the detected at least a physiological parameter; and calculating an average time from detection of indication of the state of pre-sleep relaxation to detection of entry into the hypnagogic state associated with the user as a function of the pattern.

19. The method of claim 18, wherein determining that the user is entering the hypnagogic state further comprises predicting the user's time of entry into the hypnagogic state based on the average time.

20. The method of claim 19, wherein determining that the user is entering the hypnagogic state further comprises determining the user's entry into the hypnagogic state is imminent at a time point between the indication of the state of pre-sleep relaxation and the predicted user's time of entry into the hypnagogic state.

* * * * *